United States Patent
Lalleman et al.

(10) Patent No.: US 10,716,744 B2
(45) Date of Patent: Jul. 21, 2020

(54) MULTI-STEP HAIR DYEING PROCESS USING AT LEAST ONE TITANIUM SALT AND A SYNTHETIC DIRECT DYE

(71) Applicant: L'OREAL, Paris (FR)

(72) Inventors: Boris Lalleman, Paris (FR); Alain Lagrange, Coupvray (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/735,476

(22) PCT Filed: Jun. 10, 2016

(86) PCT No.: PCT/EP2016/063360
§ 371 (c)(1),
(2) Date: Dec. 11, 2017

(87) PCT Pub. No.: WO2016/198643
PCT Pub. Date: Dec. 15, 2016

(65) Prior Publication Data
US 2019/0083376 A1    Mar. 21, 2019

(30) Foreign Application Priority Data
Jun. 12, 2015  (FR) ................................. 15 55387

(51) Int. Cl.
| | | |
|---|---|---|
| A61Q 5/10 | (2006.01) | |
| A61K 8/58 | (2006.01) | |
| A61K 8/29 | (2006.01) | |
| A61K 8/365 | (2006.01) | |
| A61Q 5/06 | (2006.01) | |
| A61K 8/22 | (2006.01) | |

(52) U.S. Cl.
CPC .................. *A61K 8/58* (2013.01); *A61K 8/22* (2013.01); *A61K 8/29* (2013.01); *A61K 8/365* (2013.01); *A61Q 5/065* (2013.01); *A61K 2800/4322* (2013.01); *A61K 2800/4324* (2013.01); *A61K 2800/58* (2013.01); *A61K 2800/884* (2013.01)

(58) Field of Classification Search
CPC .......... A61Q 5/065; A61K 8/49; A61K 8/494; A61K 8/492; A61K 2800/432; A61K 2800/884; A61K 8/898; A61K 8/22; A61K 8/361; A61K 8/29; A61K 8/365; A61K 2800/58; A61K 2800/4324
See application file for complete search history.

(56) References Cited

U.S. PATENT DOCUMENTS

| | | |
|---|---|---|
| 4,003,699 A | 1/1977 | Rose et al. |
| RE30,199 E | 1/1980 | Rose et al. |
| 5,008,093 A | 4/1991 | Merianos |
| 5,061,289 A | 10/1991 | Clausen et al. |
| 5,183,901 A | 2/1993 | Login et al. |
| 5,356,438 A | 10/1994 | Kim et al. |
| 5,380,340 A | 1/1995 | Neunhoeffer et al. |
| 5,466,263 A | 11/1995 | Herdt et al. |
| 5,534,267 A | 7/1996 | Neunhoeffer et al. |
| 5,663,366 A | 9/1997 | Neunhoeffer et al. |
| 5,708,151 A | 1/1998 | Mockli |
| 5,766,576 A | 6/1998 | Lowe et al. |
| 6,099,592 A | 8/2000 | Vidal et al. |
| 6,284,003 B1 | 9/2001 | Rose et al. |
| 6,730,789 B1 | 5/2004 | Birault et al. |
| 2001/0042276 A1 | 11/2001 | Kawasoe et al. |
| 2003/0163878 A1 | 9/2003 | Pruche |
| 2008/0233068 A1* | 9/2008 | Forbes ............... A61K 8/25 424/70.1 |
| 2010/0154143 A1* | 6/2010 | Guerin ............... A61K 8/19 8/424 |
| 2012/0110751 A1* | 5/2012 | Blackburn ........... A61K 8/19 8/421 |
| 2013/0227797 A1* | 9/2013 | Greaves .............. A61K 8/466 8/405 |

FOREIGN PATENT DOCUMENTS

| | | |
|---|---|---|
| DE | 2359399 A1 | 6/1975 |
| DE | 3843892 A1 | 6/1990 |
| DE | 4133957 A1 | 4/1993 |
| DE | 19543988 A1 | 5/1997 |
| EP | 0714954 A2 | 6/1996 |
| EP | 0770375 A1 | 5/1997 |

(Continued)

OTHER PUBLICATIONS

International Search Report for counterpart Application No. PCT/EP2016/06330, dated Jul. 26, 2016.
Hansen, C.M., "Hansen Solubility Parameters a User's Handbook," CRC Press LLC, 2000, pp. 167-185.
"Hair Preparation," Kirk Othmer Encyclopedia of Chemical Technology, pt. 4, p. 18; published online Sep. 18, 2009, DOI: 10.1002/0471238961.0801091816150812.a01.pub2., pp. 1-33.
"Hair Preparation," Ullmann's Encyclopedia of Industrial Chemistry, pt. 5.2.3 p. 21, published online: Jul. 15, 2006, DOI: 10.1002/14356007.a12_571.pub., pp. 1-46.

*Primary Examiner* — Eisa B Elhilo

(74) *Attorney, Agent, or Firm* — The Marbury Law Group, PLLC

(57) ABSTRACT

The present invention relates to a multi-step process for dyeing keratin fibres, human keratin fibres such as the hair, in which said fibres are treated with: i) at least one step i) of treating said fibres using a cosmetic composition Ci) comprising a) one or more titanium salts and b) optionally one or more particular carboxylic acids; ii) at least one step of dyeing with a colouring cosmetic composition Cii) comprising c) one or more synthetic direct dyes, preferably chosen from anionic direct dyes; iii) optionally at least one step of intermediate rinsing of said fibres, said step being performed between step i) and ii) or between step ii) and i), depending on the order in which said steps i) and ii) are performed.

20 Claims, No Drawings

(56) References Cited

FOREIGN PATENT DOCUMENTS

| | | |
|---|---:|---|
| FR | 2733749 A1 | 11/1996 |
| FR | 2801308 A1 | 5/2001 |
| FR | 2814943 A1 | 4/2002 |
| FR | 2886136 A1 | 12/2006 |
| FR | 2907672 A1 | 5/2008 |
| FR | 2976793 A1 | 12/2012 |
| GB | 1026978 A | 4/1966 |
| GB | 1153196 A | 5/1969 |
| JP | 02-019576 A | 1/1990 |
| JP | 05-163124 A | 6/1993 |
| JP | 2000-234278 A | 8/2000 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 96/15765 A1 | 5/1996 |
| WO | 00/38631 A1 | 7/2000 |
| WO | 2008/049767 A1 | 5/2008 |
| WO | 2012/175683 A2 | 12/2012 |

\* cited by examiner

MULTI-STEP HAIR DYEING PROCESS USING AT LEAST ONE TITANIUM SALT AND A SYNTHETIC DIRECT DYE

CROSS REFERENCE TO RELATED APPLICATIONS

This is a national stage application of PCT/EP2016/063360, filed internationally on Jun. 10, 2016, which claims priority to French Application No. 1555387, filed on Jun. 12, 2015, both of which are incorporated by reference herein in their entireties.

The present invention relates to a multi-step process for dyeing keratin fibres, in particular human keratin fibres such as the hair, in which said fibres are treated with:
   i) at least one step of treating said fibres with a cosmetic composition Ci) comprising a) one or more titanium salts and b) optionally one or more particular carboxylic acids;
   ii) at least one step of dyeing with a colouring cosmetic composition Cii) comprising c) one or more synthetic direct dyes, preferably chosen from anionic direct dyes;
   iii) optionally at least one step of intermediate rinsing of said fibres, said step being performed between step i) and ii) or between step ii) and i), depending on the order in which said steps i) and ii) are performed.

It is known practice to dye keratin fibres and in particular human hair with dye compositions containing direct dyes. The standard direct dyes that are used are, in particular, dyes of the nitrobenzene, anthraquinone, nitropyridine, azo, xanthene, acridine, azine or triarylmethane type, or natural dyes. These dyes may be nonionic, anionic, cationic or amphoteric.

These compositions containing one or more direct dyes, especially synthetic dyes, are applied to keratin fibres for a time necessary to obtain the desired colouring, and are then rinsed out.

The colourings that result therefrom are particularly chromatic colourings but are, however, only temporary or semi-permanent since the nature of the interactions that bind the direct dyes to the keratin fibre and their desorption from the surface and/or the core of the fibre are responsible for their weak dyeing power and/or for their poor colour build-up during colouring, and for their poor persistence especially with respect to light and washing.

This problem is all the more pronounced for anionic dyes, also known as "acid dyes". Specifically, in contrast with cationic, amphoteric and nonionic dyes, which are molecules that have affinity for keratin fibres, anionic dyes have less affinity for keratin fibres and are known to be have no persistence on keratin fibres and/or to have weaker dyeing power.

In addition, they are more readily absorbed by the skin than the hair, which has the effect of colouring the scalp during dyeing of the hair. For these reasons, anionic dyes are sparingly used as dyes for hair dyeing (see, for example, *Kirk Othmer Encyclopedia of Chemical Technology*—"Hair Preparation", pt. 4, page 18; Published Online: 18 Sep. 2009, DOI: 10.1002/0471238961.0801091816150812.a01.pub2; *Ullmann's Encyclopedia of Industrial Chemistry*, "Hair Preparation", pt 5.2.3 page 21; Published Online: 15 Jul. 2006, DOI: 10.1002/14356007.a12_571.pub2).

Moreover, it is known practice to use metals at acidic pH for dyeing keratin fibres in amounts similar to those employed for dyes using a mordanting process, which consists in preparing the fibres before performing the dyeing operation in order to obtain persistent shades (*Ullmann's Encyclopaedia* "Metal and Dyes", 2005 § 5.1, page 8). However, this process generally has the drawback of not always respecting the cosmetic nature of the keratin fibre.

WO 00/38631 describes dye compositions comprising dyes of particular naphthylazo type combined with metal salts, such as Al, Mo or Zn salts, and other metal salts including titanium salts.

However, improvements must still be made especially in terms of dyeing properties, especially in terms of power, colour build-up, chromaticity and/or persistence, preferably without leading to excessive staining of the scalp, and/or with low dyeing selectivity between the root and the end.

Progress thus remains to be made in this field for offering processes for powerful, persistent dyeing that respects the nature of the keratin fibres, starting with compositions containing synthetic direct dyes, while at the same time minimizing the problems of staining, in particular of the scalp, due especially to certain dyes such as anionic dyes.

The aim of the present invention is to provide novel processes for dyeing keratin fibres, especially human keratin fibres such as the hair, starting with synthetic direct dyes, preferably anionic dyes, which have improved dyeing properties, especially hair colouring that is powerful, chromatic and/or persistent with respect to external attacking factors, especially to shampooing, and without leading to excessive staining of the scalp. The invention is also directed towards providing hair colourings with weak selectivity between the root and the end, which do not degrade the keratin fibres, which do not impair their cosmetic properties and which stain the skin less.

This (these) aim(s) are achieved by the present invention, one subject of which is a process for dyeing keratin fibres, in particular human keratin fibres such as the hair, in which said fibres are treated, in several steps, comprising:
i) at least one step of treating said fibres using a cosmetic composition Ci) containing:
   a) one or more titanium salts: in particular, the titanium atom of said salt(s) is of oxidation state 2, 3 or 4, denoted Ti(II), Ti(III) or Ti(IV), preferably Ti(IV);
   b) optionally one or more carboxylic acid(s) of formula (I) below or a salt thereof:

in which formula (I):
   A represents a monovalent group when n has the value zero or a polyvalent group when n is greater than or equal to 1, saturated or unsaturated, cyclic or non-cyclic and aromatic or non-aromatic hydrocarbon-based group comprising from 1 to 50 carbon atoms which is optionally interrupted with one or more heteroatoms and/or optionally substituted, in particular with one or more hydroxyl and/or amino groups; preferably, A represents a monovalent ($C_1$-$C_6$)alkyl group or a polyvalent ($C_1$-$C_6$)alkylene group optionally substituted with one or more hydroxyl and/or amino groups;
   n represents an integer between 0 and 10 inclusive; preferably, n is between 0 and 5, such as between 0 and 2; and ii) at least one step of dyeing said fibres using a colouring cosmetic composition Cii) containing c) one or more synthetic direct dyes, preferably chosen from anionic direct dyes;

iii) optionally at least one step of intermediate rinsing of said fibres, said step being performed between step i) and ii) or between step ii) and i), depending on the order in which said steps i) and ii) are performed.

Preferably, composition Ci) is acidic (i.e. it has a pH of less than 7.0).

The process according to the invention has the advantage of dyeing human keratin fibres, with intense and/or persistent colouring results, and/or with good homogeneity of the colour between the root and the end of the fibres. Furthermore, the dyeing process performed makes it possible to induce very satisfactory "build-up" and/or power of the colouring, and minimizes the problems of staining of the scalp due to certain classes of dyes.

Other subjects, characteristics, aspects and advantages of the present invention will emerge even more clearly on reading the description and the examples that follow.

a) Titanium Salt(s):

The cosmetic composition Ci) used according to the treatment step i) of the process according to the invention comprises at least one or more titanium salts: in particular, the titanium atom of said salt(s) is of oxidation state 2, 3 or 4, denoted Ti(II), Ti(III) or Ti(IV), preferably Ti(IV).

The titanium salt(s) of the invention may be one or more organic or mineral titanium salts.

For the purposes of the present invention, the term "organic titanium salt" means the salts per se resulting from the action of at least one organic acid on Ti which may be of oxidation state 1, 2, 3 or 4, preferably of oxidation state 4, denoted Ti(IV).

The term "organic acid" means an acid, i.e. a compound that is capable of releasing a cation or proton $H^+$ or $H_3O^+$, in aqueous medium, which comprises at least one optionally unsaturated, linear or branched $C_1$-$C_{20}$ hydrocarbon-based chain, or a (hetero)cycloalkyl or (hetero)aryl group and at least one acid chemical function chosen in particular from carboxyl COOH, sulfuric $SO_3H$, $SO_2H$, and phosphoric $PO_3H_2$, $PO_4H_2$. In particular, the organic acid(s) for forming the organic titanium salt(s) of the invention are chosen from the carboxylic acid(s) of formula (I) as defined previously and are preferably α-hydroxy acids such as lactic acid, glycolic acid, tartaric acid or citric acid.

Preferentially, the organic titanium salt derived from the action of one or more organic acids as defined previously, preferably carboxylic acids of formula (I) as defined previously, is an optionally charged (in particular negatively charged) complex, which is complexed with one or more carboxylate groups of carboxylic acids.

Preferentially, the organic titanium salt(s) a) of the invention are chosen from those of formula (I-A) below:

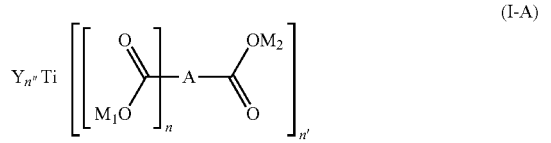

(I-A)

in which formula (I-A):

A is identical to that of formula (I)

n, n' and n", which may be identical or different, are equal to 1, 2, 3 or 4 and n'+n"=6;

$M_1$ and $M_2$, which may be identical or different, represent a cationic counterion chosen in particular from cations of an alkali metal such as Na or K or of an alkaline-earth metal such as Ca or an organic cation such as ammonium, preferably ammonium or a hydrogen atom;

$TiY_{n''}$ denoting $Ti(OH)_{n''}$, or $Ti(O)_{n''/2}$, or $Ti(OH)_{m1}(O)_{m2}$ with $m_1+m_2=n''$.

Preferentially, the radical A of compound (I-A) as defined previously represents a monovalent ($C_1$-$C_6$)alkyl or polyvalent ($C_1$-$C_6$)alkylene group optionally substituted with one or more hydroxyl groups or one or more amino groups, preferably with one or more hydroxyl groups, and n representing an integer between 0 and 5, such as between 0 and 2, inclusive; in particular, the carboxylic acid(s) used to form the organic titanium salt(s) of the invention are chosen from α-hydroxy acids and α-amino acids; preferably, the acid is chosen from citric acid, lactic acid, malic acid, tartaric acid, glycolic acid and serine, more preferentially chosen from lactic acid and glycolic acid.

Preferentially, the organic titanium salt(s) a) of the invention are chosen from those of formula (I-B) below:

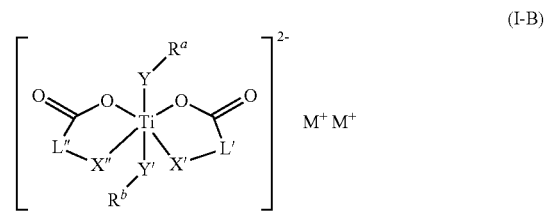

(I-B)

in which formula (I-B):

L' and L", which may be identical or different, represent a divalent (hetero)arylene, ($C_1$-$C_6$)alkylene or ($C_2$-$C_6$) alkenylene group, said alkylene and arylene groups being optionally substituted with one or more atoms or groups chosen from halo, ($C_1$-$C_4$)alkyl, hydroxyl, thiol and (di)($C_1$-$C_4$)(alkyl)amino, carboxyl, and/or optionally interrupted with one or more heteroatoms such as oxygen;

preferably, L' and L" are identical and represent a methylene or ethylene group optionally substituted with a ($C_1$-$C_4$)alkyl group;

X' and X", which may be identical or different, represent a heteroatom such as oxygen, sulfur or amino $R^c$—N with $R^c$ representing a hydrogen atom or a ($C_1$-$C_4$)alkyl group; preferably, X' and X" are identical and represent an oxygen atom;

Y and Y', which may be identical or different, are as defined for X' and X"; preferably, Y and Y' are identical and represent an oxygen atom;

$R^a$ and $R^b$, which may be identical or different, represent a hydrogen atom or a ($C_1$-$C_6$)alkyl, ($C_2$-$C_6$)alkenyl or (hetero)aryl group; particularly, $R^a$ and $R^b$, which are identical, represent a hydrogen atom or a ($C_1$-$C_4$)alkyl group, preferably hydrogen;

$M^+$, which may be identical or different, represents a cationic counterion such as a cation of an alkali metal (Na or K) or of an alkaline-earth metal (Ca) or an organic cation such as ammonium, preferably ammonium.

Preferably, the organic titanium salt(s) a) of the dyeing process are dihydroxybis(lactato)titanium(IV) salts such as those having the following formula:

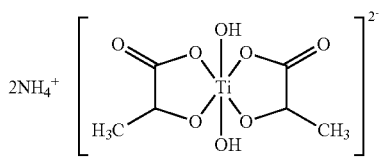

For the purposes of the present invention, the term "mineral titanium salt" means the salts per se derived from the action of a mineral acid on Ti.

The term "mineral acid" means an acid which does not comprise carbon atoms, apart from carbonic acid.

According to a particular embodiment of the invention, the titanium salt(s) a) are mineral. They are particularly chosen from titanium halides, titanium sulfates and titanium phosphates. Preferably, the mineral titanium salts are Ti(II), Ti(III) or Ti(IV) salts.

Preferably, the mineral titanium salts are Ti(III) or Ti(IV) salts.

Particularly preferably, the mineral titanium salts are Ti(IV) salts.

According to a preferred embodiment of the invention, the titanium salt(s) a) are organic titanium salts, and better still organic Ti(IV) salts. According to an advantageous embodiment of the invention, the organic Ti salt consists of a Ti(IV) atom and of 2 to 3 molar equivalents of at least one carboxylic acid of formula (I).

The titanium salt(s) a) are present in the cosmetic composition i) of the dyeing process according to the invention in a content ranging from 0.001% to 20% by weight relative to the total weight of said composition i) as defined previously.

Particularly, the organic titanium salt(s) and the mineral titanium salt(s) according to the invention are soluble in water in a proportion of at least 0.0001 g/l and better still at least 1 g/l.

b) One or More Carboxylic Acids

The cosmetic composition Ci) used according to the treatment step i) of the process according to the invention may also comprise one or more carboxylic acids.

According to an advantageous variant, the cosmetic composition Ci) used according to the treatment step i) of the process according to the invention may also comprise b) one or more carboxylic acids of formula (I) as defined previously.

More preferentially, the carboxylic acid(s) b) are different from the carboxylic acids complexed to the Ti salts, preferably glycolic acid, lactic acid, citric acid or a salt thereof. In particular, the carboxylic acid(s) b) are preferably different from the carboxylic acids complexed to the Ti salts, when the Ti salt is an organic salt derived from the action of one or more carboxylic acids as defined previously For example, if the carboxylic acid complexed to the titanium salt a) is lactic acid or the carboxylate salt thereof (lactate), the second acid b) is other than lactic acid or lactate, and may be, for example, glycolic acid.

The acid salts of formula (I) may be salts of organic or mineral bases or basifying agents e) as defined below. Preferably, the salts are sodium, ammonia or potassium salts or salts of organic amines such as alkanolamines.

The acids of formula (I) or salts thereof may be present in composition Ci) in a content ranging from 0.1% to 20% by weight relative to the total weight of said composition Ci).

c) Synthetic Direct Dye(s)

In accordance with the present invention, the colouring cosmetic composition Cii) used in the dyeing step ii) of the process according to the invention comprises c) one or more synthetic direct dyes, preferably chosen from anionic direct dyes.

The synthetic direct dye(s) that may be used in the context of the invention may be chosen from fluorescent or non-fluorescent, anionic direct dyes (also known as acid dyes), cationic direct dyes (also known as basic dyes) or neutral direct dyes.

These synthetic direct dyes are chosen in particular from those conventionally used in direct dyeing, any commonly used aromatic and/or non-aromatic dyes such as neutral, anionic (also known as acid dyes) or cationic (also known as basic dyes) nitrobenzene direct dyes, neutral, anionic (also known as acid dyes) or cationic (also known as basic dyes) azo direct dyes, neutral, anionic (also known as acid dyes) or cationic (also known as basic dyes) quinone and in particular anthraquinone direct dyes, azine, polyarylmethane such as triarylmethane, indoamine, polymethine such as styryl, porphyrin, metalloporphyrin, phthalocyanine and methine cyanine direct dyes.

Preferably, the synthetic direct dye(s) are chosen from cationic and/or neutral direct dyes, preferably chosen from nitrobenzene direct dyes, azo direct dyes, quinone and anthraquinone direct dyes, azine, polyarylmethane such as triarylmethane, indoamine, polymethine such as styryl, porphyrin, metalloporphyrin, phthalocyanine and methine cyanine direct dyes.

In the context of the present invention, the synthetic direct dye(s) are preferably present in a total amount ranging from 0.001% to 20% by weight, preferably from 0.001% to 10% by weight approximately of the total weight of the dye composition, preferably ranging from 0.005% to 5% by weight relative to the total weight of the dye composition.

According to a particular embodiment, the synthetic direct dye(s) according to the invention are chosen from anionic direct dyes or dyes commonly referred to as "acid" direct dyes or "acid dyes" on account of their affinity for alkaline substances.

The term "anionic direct dye" means any direct dye comprising in its structure at least one sulfonate $SO_3^-$ group and/or at least one carboxylate group $C(O)O-$ and optionally one or more anionic groups $G^-$ with $G^-$, which may be identical or different, representing an anionic group chosen from alkoxide $O^-$, thiolate $S^-$, carboxylate and thiocarboxylate: $C(Q)Q'^-$ with Q and Q', which may be identical or different, representing an oxygen or sulfur atom; preferably, $G^-$ represents a carboxylate, i.e. Q and Q' represent an oxygen atom.

Preferably, the anionic direct dye(s) are chosen from acidic nitro direct dyes, acidic azo dyes, acidic azine dyes, acidic triarylmethane dyes, acidic indoamine dyes, acidic anthraquinone dyes, acidic indigoids and acidic natural dyes; each of these dyes having at least one sulfonate or carboxylate group bearing a cationic counterion as defined previously; preferentially alkali metal, alkaline-earth metal or ammonium sulfonate or carboxylate.

More particularly, the dye(s) of the invention are chosen from the direct dyes of formula (VI):

$$Col^{(-)}{}_m(Q^+)_n \qquad (VI)$$

$Col^{(-)}{}_m$ represents the anionic part of the anionic direct dye or "acid" dye comprising in its structure at least one sulfonate group and/or at least one carboxylate group and comprising m anionic charges:

m and n, which may be identical or different, represent an integer between 1 and 10 inclusive;

Q$^+$, which may be identical or different, represents an organic or mineral cationic counterion preferably chosen from alkali metal or alkaline-earth metal cations such as Na$^+$ or K$^+$.

In formula (VI) of the invention, the radical Col$^{(-)}$m represents the anionic part of the "acid dyes" or of the anionic direct dyes and preferentially Col$^{(-)}$m comprises in its structure:

at least one sulfonate group and at least one (hetero)aryl group, it being understood that at least one sulfonate group is directly connected to a (hetero)aryl group, preferentially aryl such as phenyl or benzo; and optionally one or more anionic groups G$^-$ as defined previously.

According to another preferred embodiment of the invention, Col$^{(-)}$m comprises in its structure:

at least one carboxylate group and at least one (hetero)aryl group, it being understood that at least one carboxylate group is directly connected to a (hetero)aryl group, preferentially aryl such as phenyl or benzo; and optionally one or more anionic groups G$^-$ as defined previously.

According to yet another preferred embodiment of the invention, Col$^{(-)}{}_m$ comprises in its structure:

at least one sulfonate group, at least one carboxylate group and at least one (hetero)aryl group, it being understood that at least one sulfonate or carboxylate group is directly connected to a (hetero)aryl group, preferentially aryl such as phenyl or benzo; and optionally one or more anionic groups G$^-$ as defined previously.

According to a particular embodiment of the invention, the dyes of formula (VI) are such that m is equal to n.

An advantageous variant of the invention concerns the dyes of formula (VI) for which m and n are equal to 1, 2 or 3.

The preferred anionic dyes of formula (VI) of the invention are chosen from acidic nitro direct dyes, acidic azo dyes, acidic azine dyes, acidic triarylmethane dyes, acidic indoamine dyes, acidic anthraquinone dyes, acidic indigoids and acidic natural dyes; each of these dyes having at least one sulfonate or carboxylate group bearing a cationic counterion as defined previously; preferentially alkali metal, alkaline-earth metal or ammonium sulfonate or carboxylate.

As dyes according to the invention, mention may be made of the dyes of formulae (VII), (VII'), (VIII), (VIII'), (IX), (IX'), (X), (X'), (XI), (XII), (XIII) and (XIV) below:

c3a) the anionic diaryl azo dyes of formula (VII) or (VII'):

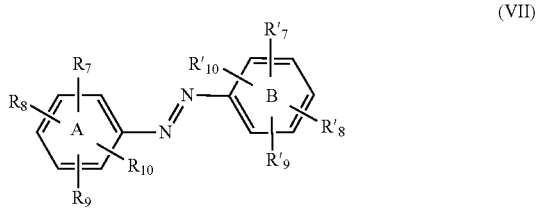

(VII)

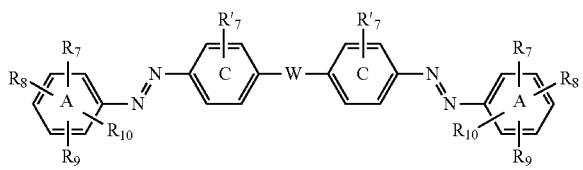

(VII')

in which formulae (VII) and (VII'):

R$_7$, R$_8$, R$_9$, R$_{10}$, R'$_7$, R'$_8$, R'$_9$ and R'$_{10}$, which may be identical or different, represent a hydrogen atom or a group chosen from: i) alkyl, ii) alkoxy, iii) alkylthio, iv) hydroxyl, v) mercapto, vi) nitro, vii) R°—C(X)—X'—, R°—X'—C(X)—, R°—X'—C(X)—X"— with R° representing a hydrogen atom or an alkyl or aryl group; X, X' and X", which may be identical or different, representing an oxygen or sulfur atom or NR with R representing a hydrogen atom or an alkyl group; viii) (O)$_2$S(O$^-$)—, M$^+$ with M$^+$ as defined previously for M or represents a cationic counterion as defined previously; ix) (O)CO$^-$—, M$^+$ with M$^+$ as defined previously; x) R"—S(O)$_2$—, with R" representing a hydrogen atom, an alkyl group, an aryl, (di)(alkyl)amino or aryl(alkyl)amino group; preferentially a phenylamino or phenyl group; xi) R'''—S(O)$_2$—X'— with R''' representing an optionally substituted alkyl or aryl group, X' as defined previously; xii) (di)(alkyl)amino; xiii) aryl(alkyl)amino optionally substituted with one or more groups chosen from nitro; nitroso; (O)$_2$S(O$^-$)—, M$^+$ and alkoxy with M$^+$ as defined previously; xiv) optionally substituted heteroaryl; preferentially a benzo thiazolyl group; xv) cycloalkyl; especially cyclohexyl, xvi) Ar—N=N— with Ar representing an optionally substituted aryl group; preferentially a phenyl optionally substituted with one or more alkyl groups, (O)$_2$S(O$^-$)—, M$^+$ or phenylamino;

or alternatively two contiguous groups R$_7$ with R$_8$ or R$_8$ with R$_9$ or R$_9$ with R$_{10}$ together form a fused benzo group A'; and R'$_7$ with R'$_8$ or R'$_8$ with R'$_9$ or R'$_9$ with R'$_{10}$ together form a fused benzo group B'; with A' and B' optionally substituted with one or more groups chosen from i) nitro; ii) nitroso; iii) (O)$_2$S(O$^-$)—, M$^+$; iv) hydroxyl; v) mercapto; vi) (di)(alkyl)amino; vii) R°—C(X)—X'—; viii) R°—X'—C(X)—; ix) R°—X'—C(X)—X"—; x) Ar—N=N— and xi) optionally substituted aryl(alkyl)amino; with M$^+$, R°, X, X', X" and Ar as defined previously;

W represents a sigma bond σ, an oxygen or sulfur atom, or a divalent radical i) —N(R)— with R as defined previously, or ii) methylene —C(R$_a$)(R$_b$)— with R$_a$ and R$_b$, which may be identical or different, representing a hydrogen atom or an aryl group, or alternatively R$_a$ and R$_b$ form, together with the carbon atom that bears them, a spiro cycloalkyl; preferentially, W represents a sulfur atom or R$_a$ and R$_b$ together form a cyclohexyl;

it being understood that formulae (VII) and (VII') comprise at least one sulfonate (O)$_2$S(O$^-$)—, Q$^+$ or carboxylate (O)C(O$^-$)—, Q$^+$ radical on one of the rings A, A', B, B' or C with R$_1$R$_2$R$_3$R$_4$ as defined previously; preferentially alkali metal, alkaline-earth metal or ammonium sulfonate or carboxylate;

As examples of dyes of formula (II), mention may be made of: Acid Red 1, Acid Red 4, Acid Red 13, Acid Red 14, Acid Red 18, Acid Red 27, Acid Red 32, Acid Red 33, Acid Red 35, Acid Red 37, Acid Red 40, Acid Red 41, Acid Red 42, Acid Red 44, Acid Red 68, Acid Red 73, Acid Red 135, Acid Red 138, Acid Red 184, Food Red 1, Food Red 13, Acid Orange 6, Acid Orange 7, Acid Orange 10, Acid Orange 19, Acid Orange 20, Acid Orange 24, Acid Yellow 9, Acid Yellow 36, Acid Yellow 199, Food Yellow 3; Acid Violet 7, Acid Violet 14, Acid Blue 113, Acid Blue 117, Acid Black 1, Acid Brown 4, Acid Brown 20, Acid Black 26, Acid Black 52, Food Black 1, Food Black 2;

and as examples of dyes of formula (VII'), mention may be made of: Acid Red 111, Acid Red 134, Acid yellow 38;

c3b) the pyrazolone anionic azo dyes of formulae (VIII) and (VIII'):

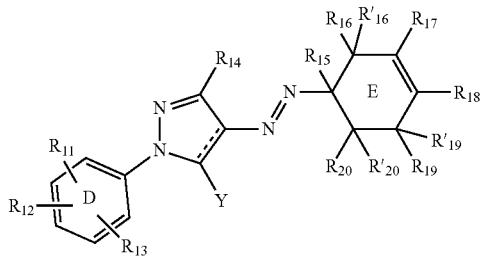

(VIII)

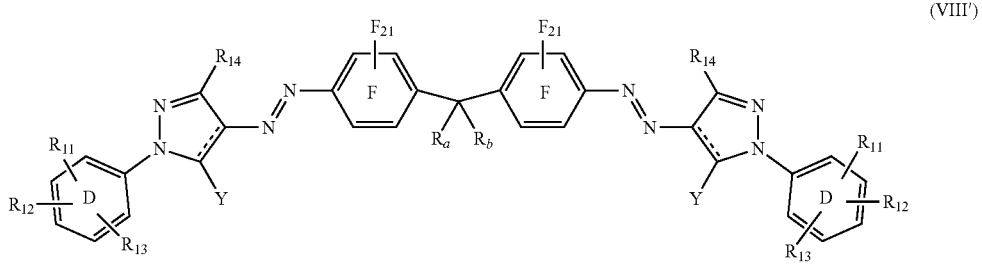

(VIII')

in which formulae (VIII) and (VIII');

$R_{11}$, $R_{12}$ and $R_{13}$, which may be identical or different, represent a hydrogen or halogen atom, an alkyl group or —(O)$_2$S(O$^-$), M$^+$ with M$^+$ as defined previously;

$R_{14}$ represents a hydrogen atom, an alkyl group or a group —C(O)O—, M$^+$ with M$^+$ as defined previously;

$R_{15}$ represents a hydrogen atom;

$R_{16}$ represents an oxo group, in which case R'$_{16}$ is absent, or alternatively $R_{15}$ with $R_{16}$ together form a double bond;

$R_{17}$ and $R_{18}$, which may be identical or different, represent a hydrogen atom or a group chosen from:
(O)$_2$S(O$^-$)—, M$^+$ with M$^+$ as defined previously;
Ar—O—S(O)$_2$— with Ar representing an optionally substituted aryl group, preferably a phenyl optionally substituted with one or more alkyl groups;

$R_{19}$ and $R_{20}$ together form either a double bond, or a benzo group D', which is optionally substituted;

R'$_{16}$, R'$_{19}$ and R'$_{20}$, which may be identical or different, represent a hydrogen atom or an alkyl or hydroxyl group;

$R_{21}$ represents a hydrogen atom or an alkyl or alkoxy group;

$R_a$ and $R_b$, which may be identical or different, are as defined previously, preferentially $R_a$ represents a hydrogen atom and $R_b$ represents an aryl group;

Y represents either a hydroxyl group or an oxo group;

---- represents a single bond when Y is an oxo group; and represents a double bond when Y represents a hydroxyl group;

it being understood that formulae (VIII) and (VIII') comprise at least one sulfonate group (O)$_2$S(O$^-$)—, Q$^+$ on one of the rings D or E or formulae (VIII) and (VIII') comprise at least one carboxylate group (O)C(O$^-$)—, Q$^+$ with Q$^+$ as defined previously; preferentially comprise at least one sulfonate group (O)$_2$S(O$^-$)—, Q$^+$ on one of the rings D or E and more particularly sulfonate;

As examples of dyes of formula (VIII), mention may be made of: Acid Red 195, Acid Yellow 23, Acid Yellow 27, Acid Yellow 76, and as examples of dyes of formula (VIII'), mention may be made of Acid Yellow 17;

c3c) the anthraquinone dyes of formulae (IX) and (IX'):

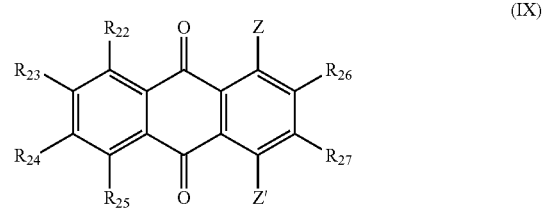

(IX)

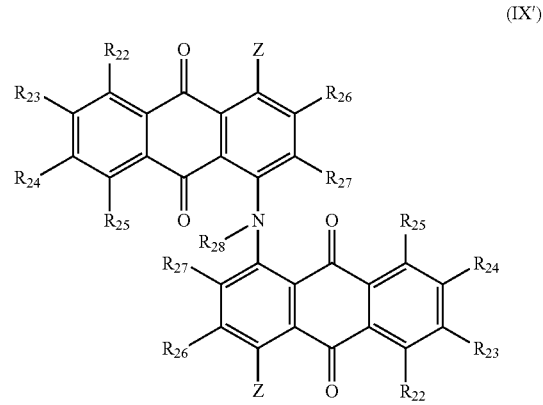

(IX')

in which formulae (IX) and (IX'):

$R_{22}$, $R_{23}$, $R_{24}$, $R_{25}$, $R_{26}$ and $R_{27}$, which may be identical or different, represent a hydrogen or halogen atom or a group chosen from i) alkyl, ii) hydroxyl, iii) mercapto, iv) alkoxy, v) alkylthio, vi) aryloxy or arylthio which is optionally substituted, preferentially substituted with one or more groups chosen from alkyl and $(O)_2S(O^-)$—, $M^+$ with $M^+$ as defined previously, vii) aryl(alkyl)amino optionally substituted with one or more groups chosen from alkyl and $(O)_2S(O^-)$—, $M^+$ with $M^+$ as defined previously, viii) (di)(alkyl)amino, ix) (di)(hydroxyalkyl)amino, x) $(O)_2S(O^-)$—, $M^+$ with $M^+$ as defined previously;

Z' represents a hydrogen atom or a group $NR_{28}R_{29}$ with $R_{28}$ and $R_{29}$, which may be identical or different, representing a hydrogen atom or a group chosen from i) alkyl, ii) polyhydroxyalkyl such as hydroxyethyl, iii) aryl optionally substituted with one or more groups, in particular alkyl such as methyl, n-dodecyl, n-butyl; $(O)_2S(O^-)$—, $M^+$ with $M^+$ as defined previously; $R°$—$C(X)$—$X'$—, $R°$—$X'$—$C(X)$—, $R°$—$X'$—$C(X)$—$X''$— with $R°$, X, X' and X'' as defined previously, preferentially $R°$ represents an alkyl group, iv) cycloakyl; especially cyclohexyl;

$Z_1$ represents a group chosen from hydroxyl and $NR'_{28}R'_{29}$ with $R'_{28}$ and $R'_{29}$, which may be identical or different, represent the same atoms or groups as $R_{28}$ and $R_{29}$ as defined previously;

it being understood that formulae (IX) and (IX') comprise at least one sulfonate group $(O)_2S(O^-)$—, $Q^+$;

As examples of dyes of formula (IX), mention may be made of: Acid Blue 25, Acid Blue 43, Acid Blue 62, Acid Blue 78, Acid Blue 129, Acid Blue 138, Acid Blue 140, Acid Blue 251, Acid Green 25, Acid Green 41, Acid Violet 42, Acid Violet 43, Mordant Red 3;

and as examples of dyes of formula (IX'), mention may be made of Acid Black 48;

c3d) the nitro dyes of formulae (X) and (X'):

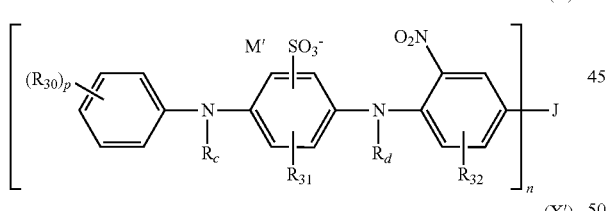

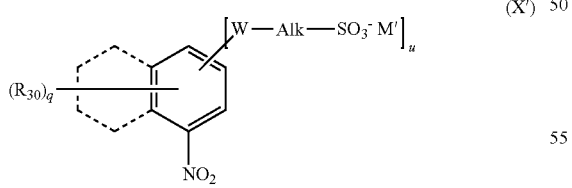

in which formulae (X) and (X'):

$R_{30}$, $R_{31}$ and $R_{32}$, which may be identical or different, represent a hydrogen or halogen atom or a group chosen from i) alkyl, ii) alkoxy optionally substituted with one or more hydroxyl groups, iii) alkylthio optionally substituted with one or more hydroxyl groups, iv) hydroxyl, mercapto, v) nitro, nitroso, vi) (poly)haloalkyl, vii) $R°$—$C(X)$—$X'$—, $R°$—$X'$—$C(X)$—, $R°$—$X'$—$C(X)$—$X''$— with $R°$; X, X' and X'' as defined previously, viii) $(O)_2S(O^-)$—, $M^+$ with $M^+$ as defined previously, ix) $(O)CO^-$—, $M^+$ with $M^+$ as defined previously, x) (di)(alkyl)amino, xi) (di)(hydroxyalkyl)amino, xii) heterocycloalkyl such as piperidino, piperazino or morpholino; in particular, $R_{30}$, $R_{31}$ and $R_{32}$ represent a hydrogen atom;

$R_c$ and $R_d$, which may be identical or different, represent a hydrogen atom or an alkyl group;

W is as defined previously; W particularly represents a group —NH—;

ALK represents a linear or branched divalent $C_1$-$C_6$ alkylene group; in particular, ALK represents a group —$CH_2$—$CH_2$—;

n is 1 or 2;

p represents an integer between 1 and 5 inclusive;

q represents an integer between 1 and 4 inclusive;

u is 0 or 1;

when n is 1, J represents a nitro or nitroso group; particularly nitro;

when n is 2, J represents an oxygen or sulfur atom, or a divalent radical —$S(O)_m$— with m representing an integer 1 or 2; preferentially, J represents a radical —$SO_2$—;

$M^+$ is as defined previously for $M^+$;

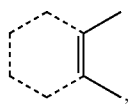

which may be present or absent, represents a benzo group optionally substituted with one or more groups $R_{30}$ as defined previously;

it being understood that formulae (X) and (X') comprise at least one sulfonate group $(O)_2S(O^-)$—, $Q^+$ or carboxylate group $(O)C(O^-)$—, $Q^+$;

As examples of dyes of formula (X), mention may be made of: Acid Brown 13 and Acid Orange 3; as examples of dyes of formula (X'), mention may be made of: Acid Yellow 1, sodium salt of 2,4-dinitro-1-naphthol-7-sulfonic acid, 2-piperidino-5-nitrobenzenesulfonic acid, 2-(4'-N,N(2"-hydroxyethyl)amino-2'-nitro)anilineethanesulfonic acid and 4-β-hydroxyethylamino-3-nitrobenzenesulfonic acid;

c3e) the triarylmethane dyes of formula (XI):

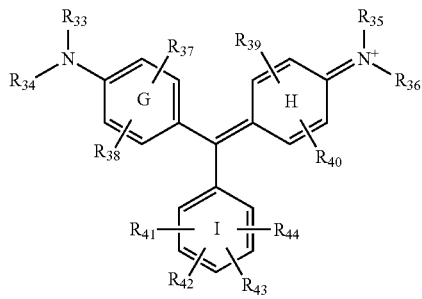

in which formula (XI):

$R_{33}$, $R_{34}$, $R_{35}$ and $R_{36}$, which may be identical or different, represent a hydrogen atom or a group chosen from alkyl, optionally substituted aryl and optionally substituted arylalkyl; particularly an alkyl group and benzyl optionally substituted with a group $(O)_mS(O^-)$—, $M^+$ with $M^+$ and m as defined previously;

$R_{37}$, $R_{38}$, $R_{39}$, $R_{40}$, $R_{41}$, $R_{42}$, $R_{43}$ and $R_{44}$, which may be identical or different, represent a hydrogen atom or a group chosen from: i) alkyl; ii) alkoxy, alkylthio; iii) (di)(alkyl)amino; iv) hydroxyl, mercapto; v) nitro, nitroso; vii) $R°$—C(X)—X'—, $R°$—X'—C(X)—, $R°$—X'—C(X)—X"— with $R°$ representing a hydrogen atom or an alkyl or aryl group; X, X' and X", which may be identical or different, representing an oxygen or sulfur atom or NR with R representing a hydrogen atom or an alkyl group; viii) $(O)_2S(O^-)$—, $M^+$ with $M^+$ representing a hydrogen atom or a cationic counterion; ix) $(O)CO^-$—, $M^+$ with $M^+$ as defined previously;

or alternatively two contiguous groups $R_{41}$ with $R_{42}$ or $R_{42}$ with $R_{43}$ or $R_{43}$ with $R_{44}$ together form a fused benzo group: I'; with I' optionally substituted with one or more groups chosen from i) nitro; ii) nitroso; iii) $(O)_2S(O^-)$—, $M^+$; iv) hydroxyl; v) mercapto; vi) (di)(alkyl)amino; vii) $R°$—C(X)—X'—; viii) $R°$—X'—C(X)—; and ix) $R°$—X'—C(X)—X"—; with $M^+$, $R°$, X, X' and X" as defined previously;

particularly, $R_{37}$ to $R_{40}$ represent a hydrogen atom, and $R_{41}$ to $R_{44}$, which may be identical or different, represent a hydroxyl group or $(O)_2S(O^-)$—, $M^+$; and when $R_{43}$ with $R_{44}$ together form a benzo group, it is preferentially substituted with a group $(O)_2S(O^-)$—;

it being understood that at least one of the rings G, H, I or I' comprises at least one sulfonate $(O)_2S(O^-)$—, $Q^+$ or carboxylate $(O)C(O^-)$—, $Q^+$ group;

As examples of dyes of formula (XI), mention may be made of: Acid Blue 1; Acid Blue 3; Acid Blue 7, Acid Blue 9; Acid Violet 49 and Acid Green 50;

c3f) the xanthene-based dyes of formula (XII):

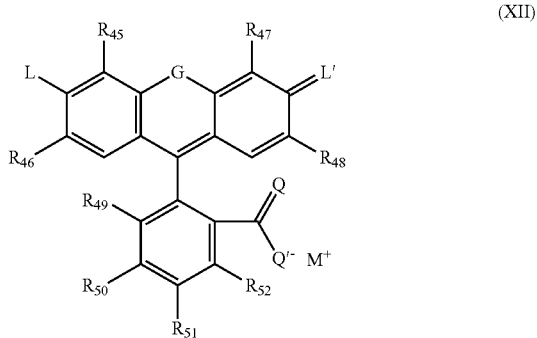

in which formula (XII):

$R_{45}$, $R_{46}$, $R_{47}$ and $R_{48}$, which may be identical or different, represent a hydrogen or halogen atom;

$R_{49}$, $R_{50}$, $R_{51}$ and $R_{52}$, which may be identical or different, represent a hydrogen or halogen atom or a group chosen from i) alkyl; ii) alkoxy, alkylthio; iii) hydroxyl, mercapto; iv) nitro, nitroso; v) $(O)_2S(O^-)$—, $M^+$ with $M^+$ representing a hydrogen atom or a cationic counterion; vi) $(O)CO^-$—, $M^+$ with $M^+$ as defined previously;

particularly $R_{53}$, $R_{54}$, $R_{55}$ and $R_{48}$ represent a hydrogen or halogen atom;

G represents an oxygen or sulfur atom or a group $NR_e$ with $R_e$ as defined previously; particularly, G represents an oxygen atom;

L represents an alkoxide $O^-$, $M^+$; a thioalkoxide $S^-$, $M^+$ or a group $NR_f$, with $R_f$ representing a hydrogen atom or an alkyl group and $M^+$ as defined previously; $M^+$ is particularly $Na^+$ or $K^+$;

L' represents an oxygen or sulfur atom or an ammonium group: $N^+R_fR_g$, with $R_f$ and $R_g$, which may be identical or different, representing a hydrogen atom, an alkyl group or optionally substituted aryl; L' represents particularly an oxygen atom or a phenylamino group optionally substituted with one or more alkyl or $(O)_mS(O^-)$—, $M^+$ groups with m and $M^+$ as defined previously;

Q and Q', which may be identical or different, represent an oxygen or sulfur atom; particularly Q and Q' represent an oxygen atom;

$M^+$ is as defined previously;

it being understood that formula (XIII) comprises at least one sulfonate group $(O)_2S(O^-)$—, $Q^+$ or carboxylate group $(O)C(O^-)$—, $Q^+$ with $Q^+$ as defined previously;

As examples of dyes of formula (XII), mention may be made of the ammonium salts derived from: Acid Yellow 73; Acid Red 51; Acid Red 87; Acid Red 92; Acid Red 95 and Acid Violet 9;

c3g) the indigoid dyes of formula (XIII):

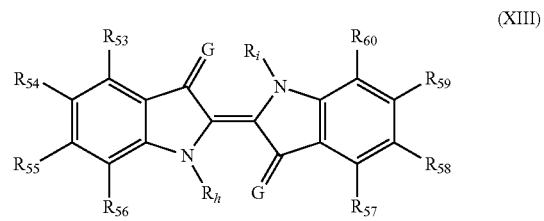

in which formula (XIII):

$R_{53}$, $R_{54}$, $R_{55}$, $R_{56}$, $R_{57}$, $R_{58}$, $R_{59}$ and $R_{60}$, which may be identical or different, represent a hydrogen atom or a group chosen from: i) alkyl; ii) alkoxy, alkylthio; iii) hydroxyl, mercapto; iv) nitro, nitroso; v) $R°$—C(X)—X'—, $R°$—X'—C(X)—, $R°$—X'—C(X)—X"— with $R°$ representing a hydrogen atom or an alkyl or aryl group; X, X' and X", which may be identical or different, representing an oxygen or sulfur atom or NR with R representing a hydrogen atom or an alkyl group; vi) $(O)_2S(O^-)$—, $M^+$ with $M^+$ as defined previously; vii) $(O)CO^-$—, $M^+$ with $M^+$ as defined previously;

G represents an oxygen or sulfur atom or a group $NR_e$ with $R_e$ as defined previously; particularly, G represents an oxygen atom;

$R_i$ and $R_h$, which may be identical or different, represent a hydrogen atom or an alkyl group;

it being understood that formula (XIII) comprises at least one sulfonate group $(O)_2S(O^-)$—, $Q^+$ or carboxylate group $(O)C(O^-)$—, $Q^+$ with $Q^+$ as defined previously;

As examples of dyes of formula (XIII), mention may be made of Acid Blue 74 and indigo carmine (or indigotine I, blue CI No. 1) is a blue dye (number E132) which is a natural extract of the indigo plant.

c3h) the quinoline-based dyes of formula (XIV):

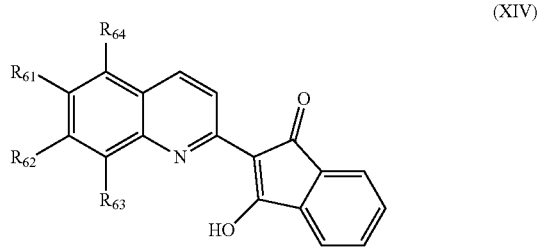

$R_{61}$ represents a hydrogen or halogen atom or an alkyl group;

$R_{62}$, $R_{63}$ and $R_{64}$, which may be identical or different, represent a hydrogen atom or a group $(O)_2S(O^-)$—, $M^+$ with $M^+$ as defined previously;

or alternatively $R_{61}$ with $R_{62}$, or $R_{61}$ with $R_{64}$, together form a benzo group optionally substituted with one or more groups $(O)_2S(O^-)$—, $M^+$ with $M^+$ representing a hydrogen atom or a cationic counterion;

it being understood that formula (IX) comprises at least one sulfonate group $(O)_2S(O^-)$—, $Q^+$ with $Q^+$ as defined previously;

As examples of dyes of formula (IX), mention may be made of the ammonium salts derived from: Acid Yellow 2, Acid Yellow 3 and Acid Yellow 5.

More particularly, the dyes of formulae (VII) to (XIV) that are useful in the invention are chosen from the salts:

| | |
|---|---|
| (C.I. 45380) | Acid Red 87 (XIV) |
| (C.I. 10316) | ammonium salts of 2,4-dinitro-1-naphthol-7-sulfonic acid (X') |
| (C.I. 10383) | Acid Orange 3 (XII) |
| (C.I. 13015) | Acid Yellow 9/Food Yellow 2 (VII) |
| (C.I. 14780) | /Direct Red 45/Food Red 13 (VII) |
| (C.I. 13711) | Acid Black 52 (VII) |
| (C.I. 13065) | Acid Yellow 36 (VII) |
| (C.I. 14700) | ammonium salt of 1-hydroxy-2-(2',4'-xylyl-5-sulfonatoazo)naphthalene-4-sulfonic acid/Food Red 1 (VII) |
| (C.I. 14720) | Acid Red 14/Food Red 3/Mordant Blue 79 (VII) |
| (C.I. 14805) | ammonium salt of 4-hydroxy-3-[(2-methoxy-5-nitrophenyl)diaza]-6-(phenylamino)naphthalene-2-sulfonic acid/Acid Brown 4 (VII) |
| (C.I. 15510) | Acid Orange 7/Pigment Orange 17/Solvent Orange 49 (VII) |
| (C.I. 15985) | Food Yellow 3/Pigment Yellow 104 (VII) |
| (C.I. 16185) | Acid Red 27/Food Red 9 (VII) |
| (C.I. 16230) | Acid Orange 10/Food Orange 4 (VII) |
| (C.I. 16250) | Acid Red 44 (VII) |
| (C.I. 17200) | Acid Red 33/Food Red 12 (VII) |
| (C.I. 15685) | Acid Red 184 (VII) |
| (C.I. 19125) | Acid Violet 3 (VII) |
| (C.I. 18055) | ammonium salt of 1-hydroxy-2-(4'-acetamidophenylazo)-8-acetamidonaphthalene-3,6-disulfonic acid/Acid Violet 7/Food Red 11 (VII) |
| (C.I. 18130) | Acid Red 135 (VII) |
| (C.I. 19130) | Acid Yellow 27(VIII) |
| (C.I. 19140) | Acid Yellow 23/Food Yellow 4 (VIII) |
| (C.I. 20170) | 4'-(sulfonato-2″,4″-dimethyl)bis(2,6-phenylazo)-1,3-dihydroxybenzene/Acid Orange 24 (VII) |
| (C.I. 20470) | ammonium salt of 1-amino-2-(4'-nitrophenylazo)-7-phenylazo-8-hydroxynaphthalene-3,6-disulfonic acid/Acid Black 1 (VII) |
| (C.I. 23266) | (4-((4-methylphenyl)sulfonyloxy)phenylazo)-2,2'-dimethyl-4-((2-hydroxy-5,8-disulfonato)naphthylazo)biphenyl/Acid Red 111 (VII') |
| (C.I. 27755) | Food Black 2 (VII) |
| (C.I. 25440) | 1-(4'-sulfonatophenylazo)-4-((2″-hydroxy-3″-acetylamino-6″,8″-disulfonato)naphthylazo)-6-sulfonatonaphthalene (tetrasodium salt)/Food Black 1 (VII) |
| (C.I. 42090) | Acid Blue 9 (XI) |
| (C.I. 60730) | Acid Violet 43 (IX) |
| (C.I. 61570) | Acid Green 25 (IX) |
| (C.I. 62045) | ammonium salt of 1-amino-4-cyclohexylamino-9,10-anthraquinone-2-sulfonic acid/Acid Blue 62 (IX) |
| (C.I. 62105) | Acid Blue 78 (IX) |
| (C.I. 14710) | ammonium salt of 4-hydroxy-3-((2-methoxyphenyl)azo)-1-naphthalenesulfonic acid/Acid Red 4 (VII) |
| | 2-piperidino-5-nitrobenzenesulfonic acid (X') |
| | 2-(4'-N,N-(2″-hydroxyethyl)amino-2'-nitro)anilineethanesulfonic acid (X') |
| | 4-β-hydroxyethylamino-3-nitrobenzene sulfonic acid (X') |
| (C.I. 42640) | Acid Violet 49 (XII) |
| (C.I. 42080) | Acid Blue 7 (XI) |
| (C.I. 58005) | 1,2-dihydroxy-3-sulfo-anthraquinone/Mordant Red 3 (IX) |
| (C.I. 62055) | 1-amino-9,10-dihydro-9,10-dioxo-4-(phenylamino) 2-anthracenesulfonic acid/Acid Blue 25 (IX) |
| (C.I. 14710) | 4-hydroxy-3-((2-methoxyphenyl)azo)-1-naphthalenesulfonic acid/Acid Red 4 (VII) |

Most of these dyes are described in particular in the Colour Index published by The Society of Dyers and Colourists, P.O. Box 244, Perkin House, 82 Grattan Road, Bradford, Yorkshire, BD1 2JBN England. The anionic dyes that are most particularly preferred are the dyes designated in the Colour Index under the code C.I. 58005 (monosodium salt of 1,2-dihydroxy-9,10-anthraquinone-3-sulfonic acid), C.I. 60730 (monosodium salt of 2-[(9,10-dihydro-4-hydroxy-9,10-dioxo-1-anthracenyl)amino]-5-methylbenzenesulfonic acid), C.I. 15510 (monosodium salt of 4-[(2-hydroxy-1-naphthalenyl)azo]benzenesulfonic acid), C.I. 15985 (disodium salt of 6-hydroxy-5-[(4-sulfophenyl)azo]-2-naphthalenesulfonic acid), C.I. 17200 (disodium salt of 5-amino-4-hydroxy-3-(phenylazo)-2,7-naphthalenedisulfonic acid), C.I. 20470 (disodium salt of 1-amino-2-(4'-nitrophenylazo)-7-phenylazo-8-hydroxy-3,6-naphthalenedisulfonic acid), C.I. 42090 (disodium salt of N-ethyl-N-[4-[[4-[ethyl[3-sulfophenyl)methyl]amino]phenyl](2-sulfophenyl) methylene]-2,5-cyclohexadien-1-ylidene]-3-sulfobenzenemethanaminium hydroxide, inner salt), C.I. 61570 (disodium salt of 2,2'-[(9,10-dihydro-9,10-dioxo-1,4-anthracenediyl)diimino]bis[5-methyl]benzenesulfonic acid).

The composition used according to the invention may of course comprise a mixture of dyes of formulae (VII), (VII'), (VIII), (VIII'), (IX), (IX'), (X), (X'), (XI), (XII), (XIII) and (XIV).

It is also possible to use compounds corresponding to the mesomeric or tautomeric forms of structures (VII) to (XIV).

More particularly, the dye(s) according to the invention are chosen from those of formulae (VII), (VIII), (IX) and (XIII), and mixtures thereof.

Preferably, the dye(s) according to the invention are chosen from the dyes of formulae (VII), (IX) and (XIII) and mixtures thereof, and preferably chosen from carmine indigo, Acid Blue 62, Acid Red 18 and Acid Black 1, and mixtures thereof.

Preferably, the anionic synthetic direct dye(s) are chosen from the dyes of formula (XIII), and in particular carmine indigo.

According to this embodiment, the total content of anionic direct dyes in the dye composition Cii) is preferably between 0.001% and 20% by weight, preferably between 0.001% and 10% by weight, preferably between 0.001% and 5% by weight, relative to the weight of composition Cii).

According to another particular embodiment of the invention, the synthetic direct dye(s) are chosen from cationic direct dyes or dyes commonly referred to as "basic" direct dyes or "basic dyes" on account of their affinity for acidic substances. The cationic dyes are preferentially chosen from hydrazono, (poly)azo, polymethine such as styryl and (poly) arylmethane dyes. More preferably, the cationic dye(s) of the invention are chosen from the hydrazono dyes of formulae (Va) and (V'a), the azo dyes (VIa) and (VI'a) and the diazo dyes (VIIa) below:

(Va)

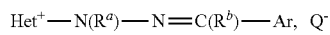
(V'a)

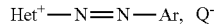
(VIa)

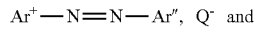
(VI'a)

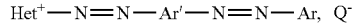
(VIIa)

formulae (Va), (V'a), (VIa), (VI'a) and (Vila) with:
- Het$^+$ representing a cationic heteroaryl radical, preferentially bearing an endocyclic cationic charge, such as imidazolium, indolium or pyridinium, optionally substituted preferentially with one or more ($C_1$-$C_8$) alkyl groups such as methyl;
- Ar$^+$ representing an aryl radical, such as phenyl or naphthyl, bearing an exocyclic cationic charge, preferentially ammonium, particularly tri($C_1$-$C_8$)alkylammonium such as trimethylammonium;
- Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;
- Ar' is an optionally substituted divalent (hetero)arylene group such as phenylene, particularly para-phenylene, or naphthalene, which are optionally substituted, preferentially with one or more ($C_1$-$C_8$)alkyl, hydroxyl or ($C_1$-$C_8$)alkoxy groups;
- Ar'' is an optionally substituted (hetero)aryl group such as phenyl or pyrazolyl, which are optionally substituted, preferentially with one or more ($C_1$-$C_8$)alkyl, hydroxyl, (di)($C_1$-$C_8$)(alkyl)amino, ($C_1$-$C_8$)alkoxy or phenyl groups;
- R$^a$ and R$^b$, which may be identical or different, represent a hydrogen atom or a ($C_1$-$C_8$)alkyl group, which is optionally substituted, preferentially with a hydroxyl group;
- or alternatively the substituent R$^a$ with a substituent of Het$^+$ and/or R$^b$ with a substituent of Ar and/or R$^a$ with R$^b$ form, together with the atoms that bear them, a (hetero)cycloalkyl;
- particularly, R$^a$ and R$^b$ represent a hydrogen atom or a ($C_1$-$C_4$)alkyl group, which is optionally substituted with a hydroxyl group;
- Q$^-$ represents an anionic counterion as defined previously.

According to a preferred variant of the invention, the cationic dyes are chosen from the polymethine dyes of formulae (VIIIa) and (VIII'a) below:

(VIIIa)

(VIII'a)

formulae (VIIIa) or (VIII'a) with:
- W$^+$ representing a cationic heterocyclic or heteroaryl group, particularly comprising a quaternary ammonium optionally substituted with one or more ($C_1$-$C_8$)alkyl groups optionally substituted especially with one or more hydroxyl groups;
- W'$^+$ representing a heterocyclic or heteroaryl as defined for W$^+$;
- Ar representing a (hetero)aryl group such as phenyl or naphthyl, optionally substituted preferentially with i) one or more halogen atoms such as chlorine or fluorine; ii) one or more groups ($C_1$-$C_8$)alkyl, preferably of $C_1$-$C_4$ such as methyl; iii) one or more hydroxyl groups; iv) one or more ($C_1$-$C_8$)alkoxy groups such as methoxy; v) one or more hydroxy($C_1$-$C_8$)alkyl groups such as hydroxyethyl, vi) one or more amino or (di) ($C_1$-$C_8$)alkylamino groups, preferably with the $C_1$-$C_4$ alkyl part optionally substituted with one or more hydroxyl groups, such as (di)hydroxyethylamino, vii) with one or more acylamino groups; viii) one or more heterocycloalkyl groups such as piperazinyl, piperidyl or 5- or 6-membered heteroaryl such as pyrrolidinyl, pyridyl and imidazolinyl;
- Ar' is a (hetero)aryl radical as defined for Ar;
- m' represents an integer between 1 and 4 inclusive, and in particular m has the value 1 or 2; more preferentially 1;
- R$^c$, R$^d$, which may be identical or different, represent a hydrogen atom or an optionally substituted ($C_1$-$C_8$) alkyl group, preferentially of $C_1$-$C_4$, or alternatively R$^○$ contiguous with W$^+$ or W'$^+$ and/or R$^d$ contiguous with Ar or Ar' and/or contiguous R$^c$ and R$^d$ form, with the atoms that bear them, a (hetero)cycloalkyl, particularly R$^○$ is contiguous with W$^+$ or W'$^+$ and forms a (hetero) cycloalkyl such as cyclohexyl;
- Q$^-$ as defined previously, preferably represents a halide or a mesylate.

Mention may be made more particularly of the azo and hydrazono dyes bearing an endocyclic cationic charge of formulae (Va), (V'a), (VIa) and (VI'a) as defined previously. More particularly those of formulae (Va), (V'a) and (VIa) derived from the dyes described in patent applications WO 95/15144, WO 95/01772 and EP-714954. Preferentially, the cationic dyes comprise an endocyclic cationic charge and have the following formula:

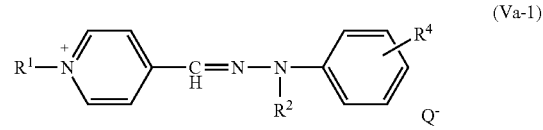
(Va-1)

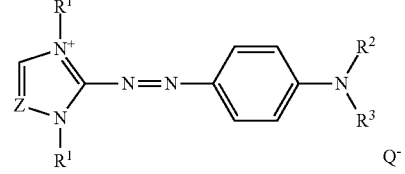
(VIa-1)

formulae (Va-1) and (VIa-1) with:
$R^1$ representing a $(C_1-C_4)$alkyl group such as methyl;
$R^2$ and $R^3$, which may be identical or different, represent a hydrogen atom or a $(C_1-C_4)$alkyl group, such as methyl; and
$R^4$ represents a hydrogen atom or an electron-donating group such as optionally substituted $(C_1-C_8)$alkyl, optionally substituted $(C_1-C_8)$alkoxy, or $(di)(C_1-C_8)$(alkyl)amino optionally substituted on the alkyl group(s) with a hydroxyl group; particularly, $R^4$ is a hydrogen atom,
Z represents a CH group or a nitrogen atom, preferentially CH,
$Q^-$ as defined previously, preferably represents a halide or a mesylate.

Particularly, the dyes of the invention are chosen from those of formula (IIIa-1) and (IVa-1) is chosen from Basic Red 51, Basic Yellow 87 and Basic Orange 31 or derivatives thereof:

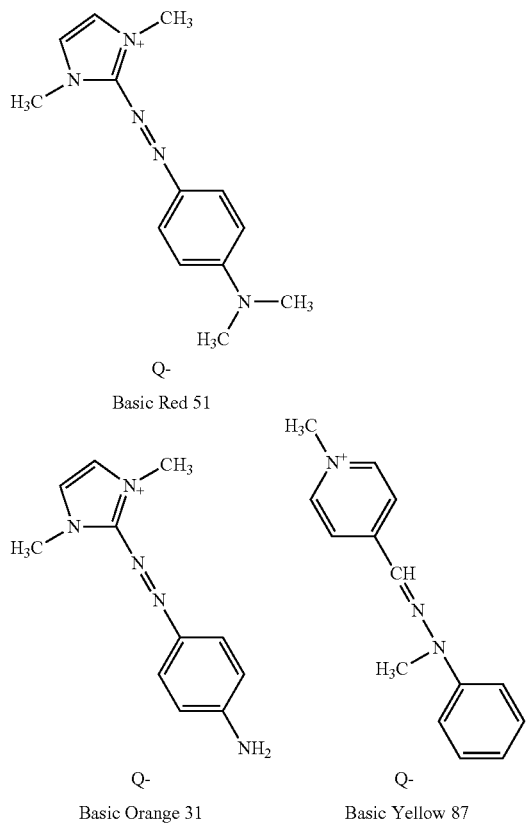

Basic Red 51

Basic Orange 31        Basic Yellow 87 with $Q^-$ as defined previously, preferably represents a halide or a mesylate.
Preferably, the synthetic direct dye(s) according to the invention are chosen from anionic direct dyes.
Preferably, the anionic direct dye(s) are chosen from the dyes of formulae (VII), (IX) and (XIII) and mixtures thereof, and in particular carmine indigo, Acid Blue 62, Acid Red 18 and Acid Black 1, and mixtures thereof.
Preferably, the cationic synthetic direct dye(s) are present in the dye composition Cii) in a total content ranging from 0.001% to 10% by weight, preferably from 0.001% to 5% of the total weight of composition Cii).

Additional Dyes:
The composition according to the invention may optionally comprise one or more additional dyes other than synthetic direct dyes. In particular, the additional dye(s) may be chosen from oxidation dyes and dyes of natural origin, preferably chosen from ortho-diphenols.
Preferably, the additional dye(s) are chosen from:
oxidation dyes preferably chosen from oxidation bases, and optionally one or more couplers; the oxidation base(s) are preferably chosen from para-phenylenediamines, bis(phenyl)alkylenediamines, para-aminophenols, ortho-aminophenols, heterocyclic bases and addition salts thereof and optionally one or more couplers, preferably chosen from meta-phenylenediamines, meta-aminophenols, meta-diphenols, naphthalene-based couplers and heterocyclic couplers, and also the addition salts thereof;
dyes of natural origin, preferably chosen from ortho-diphenols;
and mixtures thereof.

In particular, when they are present, the additional dye(s) are present in one or more cosmetic compositions that are useful in the process according to the invention (preferably the dye composition Cii)).
According to a first embodiment of the invention, the dye composition Cii) comprises one or more oxidation dyes as additional dye.

The oxidation dye precursors that may be used in the present invention are generally chosen from oxidation bases, optionally combined with one or more couplers.

The oxidation bases may preferably be chosen from para-phenylenediamines, bis(phenyl)alkylenediamines, para-aminophenols, ortho-aminophenols and heterocyclic bases, and the addition salts thereof.

Preferentially, the oxidation base(s) of the invention are chosen from para-phenylenediamines and heterocyclic bases. Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis((3-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, 2-methoxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and -3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloropara-phenylenediamine, 2-β-acetylaminoethyloxy-para-phenylenediamine and 2-methoxymethyl-para-phenylenediamine, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol and 5-acetamido-2-aminophenol, and the addition salts thereof.

Among the heterocyclic bases, mention may be made in particular of pyridine derivatives, pyrimidine derivatives and pyrazole derivatives.

Among the pyridine derivatives, mention may be made of the compounds described for example in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof, described, for example, in patent application FR 2 801 308.

Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-β-hydroxyethoxy-3-aminopyrazolo[1,5-a]pyridine and 2-(4-dimethylpiperazinium-1-yl)-3-aminopyrazolo[1,5-a]pyridine, and also the addition salts thereof.

More particularly, the oxidation bases according to the invention are chosen from 3-aminopyrazolo[1,5-a]pyridines preferably substituted in position 2 with:
 a) a (di)($C_1$-$C_6$)(alkyl)amino group, the alkyl groups possibly being substituted with one or more hydroxyl, amino or imidazolium groups;
 b) a cationic or non-cationic 5- to 7-membered heterocycloalkyl group comprising from 1 to 3 heteroatoms, optionally substituted with one or more ($C_1$-$C_6$)alkyl groups such as di($C_1$-$C_4$)alkylpiperazinium;
 c) a ($C_1$-$C_6$)alkoxy group optionally substituted with one or more hydroxyl groups, such as β-hydroxyalkoxy, and also the addition salts thereof.

Among the pyrimidine derivatives, mention may be made of the compounds described, for example, in patents DE 2359399, JP 88169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof, and the tautomeric forms thereof, when a tautomeric equilibrium exists.

Among the pyrazole derivatives mention may be made of the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(3-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(3-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(p-hydroxyethyl)amino-1-methylpyrazole, and the addition salts thereof. Preferably, the heterocyclic oxidation bases of the invention are chosen from 4,5-diaminopyrazoles such as 4,5-diamino-1-(β-hydroxyethyl)pyrazole. Use may also be made of 4,5-diamino-1-(β-methoxyethyl)pyrazole.

Use will preferably be made of a 4,5-diaminopyrazole and even more preferentially of 4,5-diamino-1-(β-hydroxyethyl)pyrazole and/or a salt thereof.

Pyrazole derivatives that may also be mentioned include diamino-N,N-dihydropyrazolopyrazolones and in particular those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one or 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt thereof.

Heterocyclic bases that will preferentially be used include 4,5-diamino-1-(β-hydroxyethyl)pyrazole and/or 2,3-diamino-6,7-dihydro-1H,5H-pyrazolo[1,2-a]pyrazol-1-one and/or a salt thereof.

The oxidation base(s) used in the context of the invention are generally present in an amount ranging from 0.001% to 10% by weight approximately, and preferably ranging from 0.005% to 5%, relative to the total weight of the dye composition.

The additional couplers that are conventionally used for the dyeing of keratin fibres are preferably chosen from meta-phenylenediamines, meta-aminophenols, meta-diphenols, naphthalene-based couplers and heterocyclic couplers, and also the addition salts thereof.

Examples that may be mentioned include 1,3-dihydroxybenzene, 1,3-dihydroxy-2-methylbenzene, 4-chloro-1,3-dihydroxybenzene, 1-hydroxy-3-aminobenzene, 2-methyl-5-aminophenol, 3-amino-2-chloro-6-methylphenol, 2-methyl-5-hydroxyethylaminophenol, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, thymol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used within the context of the invention are especially chosen from the addition salts with an acid such as the hydrochlorides, hydrobromides, sulfates, citrates, succinates, tartrates, lactates, tosylates, benzenesulfonates, phosphates and acetates.

In the context of the present invention, the coupler(s) are generally present in a total amount ranging from 0.001% to 10% by weight approximately of the total weight of the dye composition, and preferably ranging from 0.005% to 5% by weight relative to the total weight of the dye composition.

According to a second embodiment of the invention, the dye composition Cii) comprises one or more additional dyes chosen from dyes of natural origin.

The dyes of natural origin may be chosen especially from lawsone, juglone, indigo, isatin, curcumin, spinulosin, apigenidin, orceins, polyphenols or ortho-diphenols (also known as ODPs in the remainder of the description) and any extract rich in ODPs. Use may also be made of extracts or decoctions comprising these natural dyes and especially henna-based and/or indigo-based extracts or poultices.

According to a particularly preferred embodiment of the invention, the additional dye(s) of natural origin are chosen from ortho-diphenol(s) (also known as ODP(s)).

Preferably, the additional dye(s) are chosen from one or more ODPs or mixtures of compounds comprising one or more aromatic rings, at least one of which is a benzene ring substituted with at least two hydroxyl (OH) groups borne by two adjacent carbon atoms of said benzene group being present in the structure of the ortho-diphenol(s).

The aromatic ring is more particularly a fused aryl or fused heteroaromatic ring, i.e. optionally comprising one or more heteroatoms, such as benzene, naphthalene, tetrahydronaphthalene, indane, indene, anthracene, phenanthrene, indole, isoindole, indoline, isoindoline, benzofuran, dihydrobenzofuran, chroman, isochroman, chromene, isochromene, quinoline, tetrahydroquinoline and isoquinoline, said aromatic ring comprising at least two hydroxyl groups borne by two adjacent carbon atoms of the aromatic ring. Preferentially, the aromatic ring of the ortho-diphenol derivatives according to the invention is a benzene ring.

The term "fused ring" means that at least two saturated or unsaturated and heterocyclic or non-heterocyclic rings have a shared bond, i.e. at least one ring is placed side-by-side with another ring.

The ODP(s) according to the invention may or may not be salified. They may also be in aglycone form (without bonded sugar) or in the form of glycosylated compounds.

More particularly, the ODP(s) a) represent a compound of formula (II), or an oligomer, tautomer, optical isomer or geometrical isomer thereof, and also salts or solvates thereof, such as hydrates:

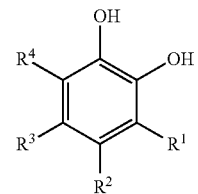

(II)

in which formula (II):
R$^1$ to R$^4$, which may be identical or different, represent:
i) a hydrogen atom, ii) a halogen atom, or a group chosen from iii) hydroxyl, iv) carboxyl, v) (C$_1$-C$_{20}$) alkyl carboxylate or (C$_1$-C$_{20}$)alkoxycarbonyl, vi) optionally substituted amino, vii) optionally substituted linear or branched (C$_1$-C$_{20}$)alkyl, viii) optionally substituted linear or branched (C$_2$-C$_{20}$)alkenyl, ix) optionally substituted cycloalkyl, x) (C$_1$-C$_{20}$)alkoxy, xi) (C$_1$-C$_{20}$)alkoxy(C$_1$-C$_{20}$)alkyl, xii) (C$_1$-C$_{20}$)alkoxyaryl, xiii) aryl which may optionally be substituted, xiv) aryl, xv) substituted aryl, xvi) heterocyclic which is saturated or unsaturated, optionally bearing a cationic or anionic charge and which is optionally substituted and/or optionally fused with an aromatic ring, preferably a benzene ring, said aromatic ring optionally being substituted, in particular with one or more hydroxyl or glycosyloxy groups, xvii) a radical containing one or more silicon atoms; or two of the substituents borne by two adjacent carbon atoms R$^1$-R$^2$, R$^2$-R$^3$ or R$^3$-R$^4$ form, together with the carbon atoms bearing them, a saturated or unsaturated and aromatic or non-aromatic ring optionally containing one or more heteroatoms and optionally fused with one or more saturated or unsaturated rings optionally containing one or more heteroatoms. In particular, the compound of formula (II) comprises from one to four rings.

A particular embodiment of the invention relates to one or more ODPs of formula (II), two adjacent substituents R$^1$-R$^2$, R$^2$-R$^3$ or R$^3$-R$^4$ of which cannot form, with the carbon atoms that bear them, a pyrrolyl radical. According to a variant, R$^2$ and R$^3$ form a pyrrolyl or pyrrolidinyl radical fused to the benzene ring bearing the two hydroxyls.

For the purposes of the present invention and unless otherwise indicated:

the saturated or unsaturated and optionally fused rings may also be optionally substituted;

the "alkyl" radicals are saturated, linear or branched, generally $C_1$-$C_{20}$, particularly $C_1$-$C_{10}$, hydrocarbon-based radicals, preferably $C_1$-$C_6$ alkyl radicals, such as methyl, ethyl, propyl, butyl, pentyl and hexyl;

the "alkenyl" radicals are unsaturated and linear or branched $C_2$-$C_{20}$ hydrocarbon-based radicals; preferably comprising at least one double bond, such as ethylene, propylene, butylene, pentylene, 2-methylpropylene and decylene;

the "aryl" radicals are monocyclic or fused or non-fused polycyclic carbon-based radicals preferentially comprising from 6 to 30 carbon atoms, at least one ring of which is aromatic; preferentially, the aryl radical is chosen from phenyl, biphenyl, naphthyl, indenyl, anthracenyl and tetrahydronaphthyl;

the "alkoxy" radicals are alkyl-oxy radicals with alkyl as defined previously, preferably $C_1$-$C_{10}$ alkyl, such as methoxy, ethoxy, propoxy and butoxy;

the "alkoxyalkyl" radicals are ($C_1$-$C_{20}$)alkoxy($C_1$-$C_{20}$) alkyl radicals, such as methoxymethyl, ethoxymethyl, methoxyethyl, ethoxyethyl, etc.;

the "cycloalkyl" radicals are $C_4$-$C_8$ cycloalkyl radicals, preferably cyclopentyl and cyclohexyl radicals; the cycloalkyl radicals may be substituted cycloalkyl radicals, in particular substituted with alkyl, alkoxy, carboxylic acid, hydroxyl, amine and ketone groups;

the "alkyl" or "alkenyl" radicals, when they are "optionally substituted", may be substituted with at least one atom or group borne by at least one carbon atom chosen from: i) halogen; ii) hydroxyl; iii) ($C_1$-$C_2$)alkoxy; iv) ($C_1$-$C_{10}$)alkoxycarbonyl; v) (poly)hydroxy($C_2$-$C_4$) alkoxy; vi) amino; vii) 5- or 6-membered heterocycloalkyl; viii) optionally cationic 5- or 6-membered heteroaryl, preferably imidazolium, optionally substituted with a ($C_1$-$C_4$)alkyl radical, preferably methyl; ix) amino substituted with one or two identical or different $C_1$-$C_6$ alkyl radicals optionally bearing at least: a) one hydroxyl group, b) one amino group optionally substituted with one or two optionally substituted ($C_1$-$C_3$) alkyl radicals, it being possible for said alkyl radicals to form, with the nitrogen atom to which they are attached, a saturated or unsaturated and optionally substituted 5- to 7-membered heterocycle optionally comprising at least one other nitrogen or non-nitrogen heteroatom, c) a quaternary ammonium group —N⁺R'R"R'", M⁻ for which R', R" and R'", which may be identical or different, represent a hydrogen atom or a $C_1$-$C_4$ alkyl group; and M⁻ represents the counterion of the corresponding organic acid, mineral acid or halide, d) or one optionally cationic 5- or 6-membered heteroaryl radical, preferentially imidazolium, optionally substituted with a ($C_1$-$C_4$)alkyl radical, preferably methyl; x) acylamino (—N(R)—C(O)—R') in which the R radical is a hydrogen atom or a ($C_1$-$C_4$)alkyl radical optionally bearing at least one hydroxyl group and the R' radical is a $C_1$-$C_2$ alkyl radical; a carbamoyl (($R)_2$N—C(O)—) radical in which the R radicals, which may be identical or different, represent a hydrogen atom or a ($C_1$-$C_4$)alkyl radical optionally bearing at least one hydroxyl group; xi) alkylsulfonylamino (R'—S(O)$_2$—N(R)—) in which the R radical represents a hydrogen atom or a ($C_1$-$C_4$)alkyl radical optionally bearing at least one hydroxyl group and the R' radical represents a ($C_1$-$C_4$)alkyl radical, a phenyl radical; xii) aminosulfonyl (($R)_2$N—S(O)$_2$—) in which the R radicals, which may be identical or different, represent a hydrogen atom or a ($C_1$-$C_4$)alkyl radical optionally bearing at least one group chosen from a) hydroxyl, b) carboxyl —C(O)—OH in the acid or salified form (preferably salified with an alkali metal or a substituted or unsubstituted ammonium); xiii) cyano; xiv) nitro; xv) carboxyl or glycosylcarbonyl; xvi) phenylcarbonyloxy optionally substituted with one or more hydroxyl groups; xvii) glycosyloxy; and phenyl group optionally substituted with one or more hydroxyl groups;

the "aryl" or "heterocyclic" radicals or the aryl or heterocyclic part of the radicals, when they are "optionally substituted", may be substituted with at least one atom or group borne by at least one carbon atom chosen from:

i) ($C_1$-$C_{10}$)alkyl, preferably $C_1$-$C_8$ alkyl, optionally substituted with one or more radicals chosen from the following radicals: hydroxyl, ($C_1$-$C_2$)alkoxy, (poly)hydroxy($C_2$-$C_4$)alkoxy, acylamino, amino substituted with two identical or different $C_1$-$C_4$ alkyl radicals optionally bearing at least one hydroxyl group or it being possible for the two radicals to form, with the nitrogen atom to which they are attached, a saturated or unsaturated and optionally substituted 5- to 7-membered, preferably 5- or 6-membered, heterocycle optionally comprising another nitrogen or non-nitrogen heteroatom; ii) halogen; iii) hydroxyl; iv) $C_1$-$C_2$ alkoxy; v) $C_1$-$C_{10}$ alkoxycarbonyl; vi) (poly)hydroxy($C_2$-$C_4$)alkoxy; vii) amino; viii) 5- or 6-membered heterocycloalkyl; ix) optionally cationic 5- or 6-membered heteroaryl, preferably imidazolium, optionally substituted with a ($C_1$-$C_4$)alkyl radical, preferably methyl; x) amino substituted with one or two identical or different $C_1$-$C_6$ alkyl radicals optionally bearing at least: a) one hydroxyl group, b) one amino group optionally substituted with one or two optionally substituted $C_1$-$C_3$ alkyl radicals, it being possible for said alkyl radicals to form, with the nitrogen atom to which they are attached, a saturated or unsaturated and optionally substituted 5- to 7-membered heterocycle optionally comprising at least one other nitrogen or non-nitrogen heteroatom, c) one quaternary ammonium group —N⁺R'R"R'", M⁻ for which R', R" and R'", which may be identical or different, represent a hydrogen atom or a $C_1$-$C_4$ alkyl group; and M⁻ represents the counterion of the corresponding organic acid, mineral acid or halide, d) one optionally cationic 5- or 6-membered heteroaryl radical, preferably imidazolium, optionally substituted with a ($C_1$-$C_4$)alkyl radical, preferentially methyl; xi) acylamino (—N(R)—C(O)—R') in which the radical R is a hydrogen atom or a $C_1$-$C_4$ alkyl radical optionally bearing at least one hydroxyl group and the radical R' is a $C_1$-$C_2$ alkyl radical; xii) carbamoyl (($R)_2$N—C(O)—) in which the R radicals, which may be identical or different, represent a hydrogen atom or a $C_1$-$C_4$ alkyl radical optionally bearing at least one hydroxyl group; xiii) alkylsulfonylamino (R'S(O)$_2$—N(R)—) in which the radical R represents a hydrogen atom or a $C_1$-$C_4$ alkyl radical optionally bearing at least one hydroxyl group and the radical R' represents a $C_1$-$C_4$ alkyl radical, a phenyl radical; xiv) aminosulfonyl (($R)_2$N—S(O)$_2$—) in which the radicals R, which may be identical or different, represent a hydrogen atom or a C$_1$-C$_4$ alkyl radical optionally bearing at least one hydroxyl group; xv) carboxyl in the acid or salified form (preferably salified with an alkali metal or a substituted or unsubstituted ammonium); xvi) cyano; xvii) nitro; xviii) polyhaloalkyl, preferentially trifluoromethyl; xix) a glycosylcarbonyl; xx) a phenylcarbonyloxy group optionally substituted with one or more hydroxyl groups; xxi) a glycosyloxy group; and xxii) a phenyl group optionally substituted with one or more hydroxyl groups;

for the purposes of the present invention, the term "glycosyl" radical means a radical derived from a mono- or polysaccharide;

the radicals "containing one or more silicon atoms" are preferably polydimethylsiloxane, polydiphenylsiloxane, polydimethylphenylsiloxane or stearoxy dimethicone radicals;

the "heterocyclic" radicals are radicals comprising, in at least one ring, one or more heteroatoms chosen in particular from O, N and S, preferably O or N, optionally substituted in particular with one or more alkyl, alkoxy, carboxyl, hydroxyl, amine or ketone groups. These rings may comprise one or more oxo groups on the carbon atoms of the heterocycle; mention may in particular be made, among the heterocyclic radicals that may be used, of furyl, pyranyl, pyrrolyl, imidazolyl, pyrazolyl, pyridyl or thienyl groups; even more preferably, the heterocyclic groups are fused groups, such as benzofuryl, chromenyl, xanthenyl, indolyl, isoindolyl, quinolyl, isoquinolyl, chromanyl, isochromanyl, indolinyl, isoindolinyl, coumarinyl or isocoumarinyl groups, it being possible for these groups to be substituted, in particular with one or more OH groups.

The ODP(s) that are useful in the process of the invention as additional dyes may be natural or synthetic. Among the natural ODPs are compounds that may be present in nature and that are reproduced by chemical (semi)synthesis.

The salts of the ODPs of the invention may be salts of acids or of bases. The acids may be mineral or organic. Preferably, the acid is hydrochloric acid, which results in chlorides.

According to another embodiment, the dye composition used in the process according to the invention comprises one or more natural ODPs as additional dyes.

More particularly, the ODP(s) that may be used as additional dyes in the process of the invention according to a) are in particular:

flavanols, for instance catechin and epicatechin gallate,
flavonols, for instance quercetin,
anthocyanidins, for instance cyanidin, delphinidin and petunidin,
anthocyanins or anthocyans, for instance myrtillin,
ortho-hydroxybenzoates, for example gallic acid salts,
flavones, for instance luteolin,
hydroxystilbenes, for example 3,3',4,5'-tetrahydroxystilbene, optionally oxylated (for example glucosylated),
3,4-dihydroxyphenylalanine and derivatives thereof,
2,3-dihydroxyphenylalanine and derivatives thereof,
4,5-dihydroxyphenylalanine and derivatives thereof,
dihydroxycinnamates, such as caffeic acid and chlorogenic acid,
ortho-polyhydroxycoumarins,
ortho-polyhydroxyisocoumarins,
ortho-polyhydroxycoumarones,
ortho-polyhydroxyisocoumarones,
ortho-polyhydroxychalcones,
ortho-polyhydroxychromones,
quinones,
hydroxyxanthones,
1,2-dihydroxybenzene and derivatives thereof,
1,2,4-trihydroxybenzene and derivatives thereof,
1,2,3-trihydroxybenzene and derivatives thereof,
2,4,5-trihydroxytoluene and derivatives thereof,
proanthocyanidins and especially the proanthocyanidins A1, A2, B1, B2, B3 and C1,
chroman and chromene compounds,
proathocyanins,
tannic acid,
ellagic acid,
and mixtures of the preceding compounds.

According to the invention, the term "chromene or chroman" ODP compounds means ODPs which comprise in their structure at least one bicycle of formula (A) below:

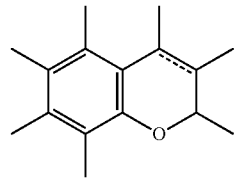

(A)

the endocyclic bond ---- representing a carbon-carbon single bond or else a carbon-carbon double bond, as illustrated by formula (A1) below, denoting the chromene family, and formula (A2) below, denoting the chroman family:

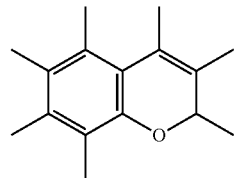

(A1)

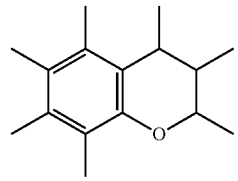

(A2)

More particularly, the ODPs of the invention are of formula (A) and are preferably chosen from the dyes of the following formulae:

formula (III), comprising, in its structure, the bicycle of formula (A2):

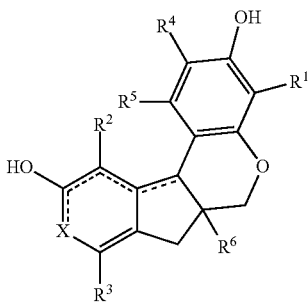

(III)

and also the tautomeric and/or mesomeric forms thereof, the stereoisomers thereof, the addition salts thereof with a cosmetically acceptable acid or base, and the hydrates thereof;
in which formula (III):
- - - - represents a carbon-carbon single bond or a carbon-carbon double bond, the sequence of these - - - - bonds denoting two carbon-carbon single bonds and two carbon-carbon double bonds, said bonds being conjugated,
X represents a group:

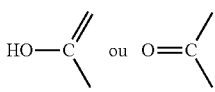

$R^1$, $R^2$, $R^3$, $R^4$, $R^5$ and $R^6$, which may be identical or different, represent a hydrogen atom, a hydroxyl group, an optionally substituted alkyl group, an optionally substituted alkoxy group or an optionally substituted acyloxy group; and
formula (IV), comprising, in its structure, the bicycle of formula (A1):

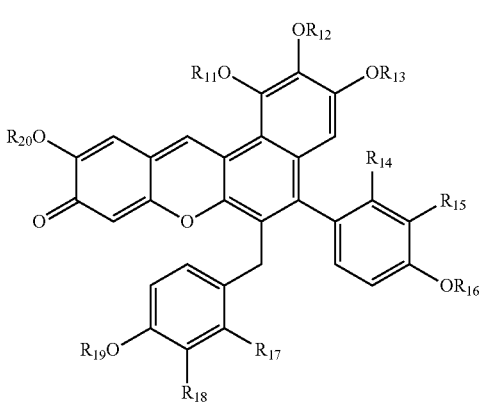

(IV)

and also the tautomeric and/or mesomeric forms thereof, the stereoisomers thereof, the addition salts thereof with a cosmetically acceptable acid or base, and the hydrates thereof;
in which formula (IV):
$R_{11}$, $R_{12}$, $R_{13}$, $R_{16}$, $R_{19}$ and $R_{20}$, which may be identical or different, represent a hydrogen atom or a $C_1$-$C_4$ alkyl radical, and $R_{14}$, $R_{15}$, $R_{17}$ and $R_{18}$, which may be identical or different, represent a hydrogen atom, a hydroxyl radical or a $C_1$-$C_4$ alkoxy radical.

As regards the ortho-diphenols of formula (III) as defined above, they may be found in two tautomeric forms denoted (IIIa) and (IIIb):

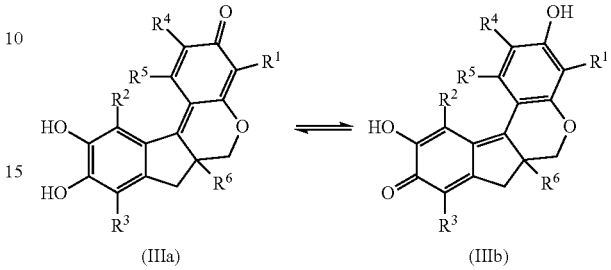

(IIIa)      (IIIb)

The alkyl radicals mentioned in the preceding definitions of the substituents are saturated and linear or branched hydrocarbon-based radicals, generally $C_1$-$C_{20}$, particularly $C_1$-$C_{10}$, preferably $C_1$-$C_{10}$, hydrocarbon-based radicals, such as methyl, ethyl, propyl, butyl, pentyl and hexyl.

The alkoxy radicals are alkyl-oxy radicals with the alkyl radicals as defined above and preferably the alkoxy radicals are $C_1$-$C_{10}$ alkoxy radicals, such as methoxy, ethoxy, propoxy and butoxy.

The alkyl or alkoxy radicals, when they are substituted, may be substituted with at least one substituent borne by at least one carbon atom chosen from: i) a halogen atom or ii) a hydroxyl group; iii) a $C_1$-$C_2$ alkoxy group; iv) a $C_1$-$C_{10}$ alkoxycarbonyl group; v) a (poly)hydroxy($C_2$-$C_4$)alkoxy group; vi) an amino group; vii) a 5- or 6-membered heterocycloalkyl group; viii) an optionally cationic 5- or 6-membered heteroaryl group, preferably imidazolium, optionally substituted with a ($C_1$-$C_4$)alkyl radical, preferably methyl; ix) an amino radical substituted with one or two identical or different $C_1$-$C_6$ alkyl radicals optionally bearing at least: a) one hydroxyl group,
b) one amino group optionally substituted with one or two optionally substituted $C_1$-$C_3$ alkyl radicals, it being possible for said alkyl radicals to form, with the nitrogen atom to which they are attached, a saturated or unsaturated and optionally substituted 5- to 7-membered heterocycle optionally comprising at least one other nitrogen or non-nitrogen heteroatom, c) one quaternary ammonium group —N⁺R'R"R'", M⁻ for which R', R" and R'", which may be identical or different, represent a hydrogen atom or a $C_1$-$C_4$ alkyl group and M⁻ represents the counterion of the corresponding organic acid, mineral acid or halide, d) or one optionally cationic 5- or 6-membered heteroaryl radical, preferentially imidazolium, optionally substituted with a ($C_1$-$C_4$)alkyl radical, preferentially methyl; x) an acylamino (—NR—COR') radical in which the R radical is a hydrogen atom or a $C_1$-$C_4$ alkyl radical optionally bearing at least one hydroxyl group and the R' radical is a $C_1$-$C_2$ alkyl radical; xi) a carbamoyl (($R)_2$N—CO—) radical in which the R radicals, which may be identical or different, represent a hydrogen atom or a $C_1$-$C_4$ alkyl radical optionally bearing at least one hydroxyl group; xii) an alkylsulfonylamino (R'$SO_2$—NR—) radical in which the R radical represents a hydrogen atom or a $C_1$-$C_4$ alkyl radical optionally bearing at least one hydroxyl group and the R' radical represents a $C_1$-$C_4$ alkyl radical, a phenyl radical; xiii) an aminosulfonyl (($R)_2N$—$SO_2$—) radical in which the R radicals, which may be identical or different, represent a hydrogen atom or a $C_1$-$C_4$ alkyl radical optionally bearing at least one hydroxyl group; xiv) a carboxyl radical in the acid or salified form (preferably salified with an alkali metal or a substituted or unsubstituted ammonium); xv) a cyano group; xvi) a nitro group; xvii) a carboxyl or glycosylcarbonyl group; xviii) a phenylcarbonyloxy group optionally substituted with one or more hydroxyl groups; xix) a glycosyloxy group; and xx) a phenyl group optionally substituted with one or more hydroxyl groups.

The term "glycosyl radical" means a radical derived from a monosaccharide or polysaccharide.

Preferably, the alkyl or alkoxy radicals of formula (III) are unsubstituted.

According to a particular embodiment of the invention, the dyes of formula (III) comprise a radical $R_6$ representing a hydroxyl group.

Another particular embodiment of the invention relates to the ODPs of formula (III) for which the radical $R_7$ represents a hydrogen atom or a hydroxyl group.

More particularly, the composition according to the invention may comprise one or more ODPs of formula (III) chosen from haematoxylin, haematein, brazilin and brazilein.

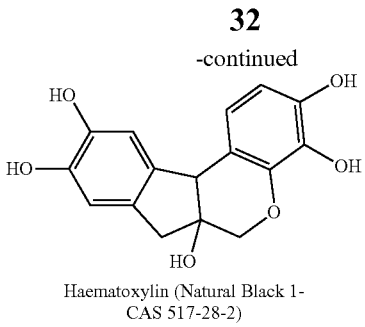

Haematoxylin (Natural Black 1-
CAS 517-28-2)

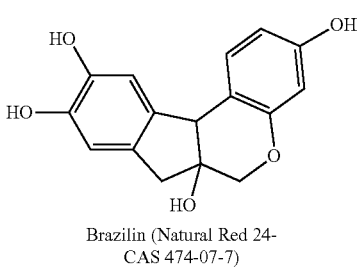

Brazilin (Natural Red 24-
CAS 474-07-7)

Brazilein is a conjugated form of a chroman compound of formula (A2). The tautomeric structures (IIIa) and (IIIb) illustrated above are found in the scheme below.

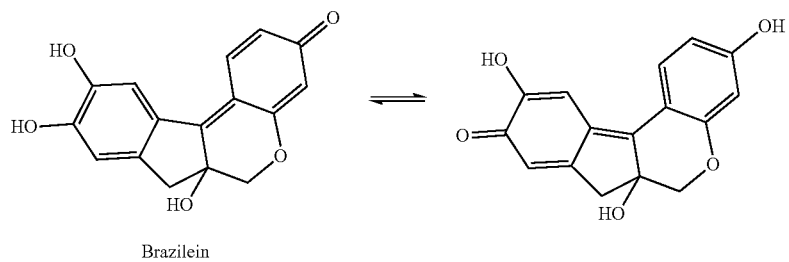 [SMILES: O=C1C=CC2=C3c4cc(O)c(O)cc4CC3(O)COC2=C1 ; O=C1C=C2CC3(O)COc4cc(O)ccc4C3=C2C=C1O]

Brazilein

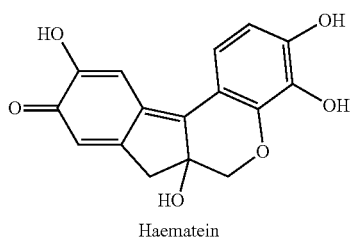

Haematein

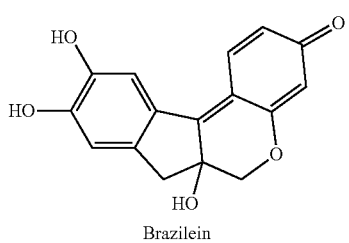

Brazilein

Among the ODPs of haematoxylin/haematein and brazilin/brazilein type, examples that may be mentioned include haematoxylin (Natural Black 1 according to the INCI name) and brazilin (Natural Red 24 according to the INCI name), dyes of the indochroman family, which are commercially available. The latter dyes may exist in an oxidized form and may be obtained synthetically or by extraction from plants or vegetables known to be rich in these dyes.

The ODPs of formula (III) may be used in the form of extracts. Use may be made of the following plant extracts (genus and species): *Haematoxylon campechianum, Haematoxylon brasiletto, Caesalpinia echinata, Caesalpinia sappan, Caesalpinia spinosa* and *Caesalpinia brasiliensis.*

The extracts are obtained by extracting the various plant parts, for instance the roots, the wood, the bark or the leaves.

According to one particular embodiment of the invention, the natural ODPs are of formula (I) and are obtained from logwood, pernambuco wood, *sappan* wood and Brazil wood.

According to a particular embodiment of the invention, the ODPs are of formula (IV), preferably those for which $R_{11}$ and $R_{13}$ represent an alkyl radical, preferably methyl.

Preferably, $R_{12}$, $R_{16}$, $R_{19}$, and $R_{20}$ denote, independently of each other, a hydrogen atom or an alkyl radical, preferably methyl.

Preferably, $R_{14}$ and $R_{17}$ denote, independently of each other, a hydrogen atom or an alkoxy radical, preferably methoxy.

Preferably, $R_{18}$ and $R_{15}$ denote, independently of each other, a hydrogen atom, a hydroxyl radical or an alkoxy radical, preferably methoxy.

A first particularly preferred family of ODPs that are suitable for use in the present invention is that of the dyes corresponding to formula (II) above for which $R_{12}$, $R_{15}$, $R_{16}$, $R_{17}$, $R_{19}$ and $R_{20}$ each represent a hydrogen atom. $R_{11}$ and $R_{13}$ each represent a methyl radical and $R_{14}$ represents a methoxy radical.

The preferred ODPs of this first family include those for which $R_{18}$ represents a methoxy radical (santalin B) or a hydroxyl radical (santalin A).

A second particularly preferred family of ODPs that are suitable for use in the present invention is that of the dyes corresponding to the formula (IV) above for which:

$R_{11}$ and $R_{13}$ each represent a methyl radical, $R_{17}$ represents a methoxy radical.

A preferred dye of this second family is that for which, in addition, $R_{19}$ represents a methyl radical, $R_{20}$, $R_{12}$, $R_{14}$, $R_{13}$ and $R_{16}$ each represent a hydrogen atom and $R_{15}$ represents a hydroxyl radical (santarubin A).

A second preferred dye of this second family is that for which $R_{18}$, $R_{20}$, $R_{12}$, $R_{14}$ and $R_{16}$ represent a hydrogen atom, $R_{15}$ represents a methoxy radical and $R_{19}$ represents a methyl radical (santarubin B).

A third preferred family of ODPs of this second family is that for which $R_{20}$, $R_{12}$, $R_{14}$, $R_{15}$, $R_{16}$ and $R_{19}$ represent hydrogen and $R_{18}$ represents a hydroxyl radical (santarubin C).

The preferred ODP of this second family is that for which $R_{15}$ represents a methoxy radical, $R_{18}$ and $R_{14}$ represent a hydrogen atom and $R_{20}$, $R_{12}$, $R_{16}$ and $R_{19}$ represent a methyl radical (tetra-O-methylsantarubin).

The ODP(s) of formula (IV) may be used in the form of extracts. Use may be made of plant extracts of red woods, bringing together generally the species of red woods from Asia and West Africa of the genus *Pterocarpus* and of the genus *Baphia*. These woods are, for example, *Pterocarpus santalinus, Pterocarpus osun, Pterocarpus soyauxii, Pterocarpus erinaceus, Pterocarpus indicus* or *Baphia nitida*. These woods may also be called padauk, sandalwood, narra wood, camwood or bar wood.

Thus, extracts that may be used, comprising ODPs of formula (II), in the present invention may be obtained, for example, from red sandalwood (*Pterocarpus santalinus*) by aqueous basic extraction, such as the product sold under the trade name Santal Concentré SL 709C by the company COPIAA, or also by means of solvent extraction of sandalwood powder, such as the product sold under the trade name Santal Poudre SL PP by the same company COPIAA. Mention may also be made of the aqueous/alcoholic extract of powdered red sandalwood from the company Alban Muller.

Extracts also suitable for the present invention can be obtained from woods such as camwood (*Baphia nitida*) or also bar wood (*Pterocarpus soyauxii, Pterocarpus erinaceus*): the latter is thus split up and then ground: a conventional alcoholic extraction or one by percolation is subsequently carried out on this ground material in order to collect a pulverulent extract particularly suitable for the implementation of the present invention.

The ODP salts of formulae (III) and (IV) of the invention may be salts of acids or bases that are cosmetically acceptable.

The acids may be mineral or organic. Preferably, the acid is hydrochloric acid, which results in chlorides.

The bases may be mineral or organic. In particular, the bases are alkali metal hydroxides such as sodium hydroxide which leads to sodium salts.

Preferably, the ODP(s) of formulae (III) and (IV) included in the composition according to the invention are derived from plant extracts. Use may also be made of mixtures of plant extracts.

The natural extracts of ODPs according to the invention may be in the form of powders or liquids. Preferably, the extracts are in powder form.

In particular, the ODPs of the invention are included among catechin, quercetin, brazilin, haematein, haematoxylin, chlorogenic acid, caffeic acid, gallic acid, catechol, L-DOPA, pelargonidin, cyanidin, (−)-epicatechin, (−)-epigallocatechin, (−)-epigallocatechin 3-gallate (EGCG), (+)-catechin, isoquercetin, pomiferin, esculetin, 6,7-dihydroxy-3-(3-hydroxy-2,4-dimethoxyphenyl)coumarin, santalin AC, mangiferin, butein, maritimetin, sulfuretin, robtein, betanidin, pericampylinone A, theaflavin, proanthocyanidin A2, proanthocyanidin B2, proanthocyanidin C1, procyanidins DP 4-8, tannic acid, purpurogallin, 5,6-dihydroxy-2-methyl-1,4-naphthoquinone, alizarin, wedelolactone, variegatic acid, gomphidic acid, xerocomic acid and carnosol, and natural extracts containing them.

Preferably, the ODPs of the invention are chromenes or chromans and are chosen from haematein, haematoxylin, brazilein, brazilin and santalin A.

The term "carboxylate" is understood to mean carboxylic acid salt.

When the dye precursors have D and L forms, both forms may be used in the compositions according to the invention, as may the racemates.

According to one embodiment, the natural ODPs are derived from extracts of animals, bacteria, fungi, algae, plants and fruits, used in their entirety or partially. In particular regarding plants, the extracts are derived from fruit, including citrus fruit, from vegetables, from trees and from shrubs. Use may also be made of mixtures of these extracts, which are rich in ODPs as defined above.

Preferably, the natural ODP(s) of the invention are derived from extracts of plants or plant parts.

The extracts are obtained by extraction of various plant parts, for instance the root, the wood, the bark, the leaf, the flower, the fruit, the seed, the pod or the peel.

Among the plant extracts, mention may be made of extracts of tea leaves and of rose.

Among the fruit extracts, mention may be made of extracts of apple, of grape (in particular of grape seed) or extracts of cocoa beans and/or pods.

Among the vegetable extracts, mention may be made of extracts of potato or of onion peel.

Among the extracts of tree wood, mention may be made of extracts of pine bark and extracts of logwood.

Use may also be made of mixtures of plant extracts.

According to a particular embodiment of the invention, the ortho-diphenol derivative(s) are natural extracts, rich in ODPs.

According to a preferred embodiment, the dye(s) of the invention are solely natural extracts.

Preferentially, the dye(s) according to the invention are chosen from catechin, quercetin, haematein, haematoxylin, brazilin, brazilein, gallic acid and tannic acid, and natural extracts containing them chosen from grape marc, pine bark, green tea, onion, cocoa bean, logwood, redwood and gall nut.

More preferentially, the ODP(s) of the invention are chosen from:
haematein, brazilein, gallic acid or tannic acid, when the dyeing process does not use a chemical oxidizing agent;
or else
haematoxylin, brazilin, gallic acid or tannic acid, when the dyeing process uses a chemical oxidizing agent.

The natural extracts according to the invention may be in the form of powders or liquids. Preferably, the extracts of the invention are provided in the form of powders.

When it is (they are) present, the additional dye(s) of natural origin are present in the dye composition Cii) preferably in a total content ranging from 0.001% to 10% by weight, preferably from 0.001% to 5% of the total weight of composition Cii).

As regards the pure dyes, especially the pure ODPs, the content in the composition(s) containing them (preferably the dye composition Cii)) is preferably between 0.001% and 5% by weight of each of the compositions containing them.

As regards the extracts, the content in the composition(s) (preferably the dye composition Cii)) containing the extracts per se is preferably between 0.1% and 20% by weight of each of these compositions, and better still between 0.5% and 10% by weight of the compositions containing them.

d) Liquid Organic Compound with a Hansen Solubility Parameter Value $\delta H$ of Greater than 0 and Less than 16 $MPa^{1/2}$.

According to an advantageous embodiment of the invention, one of the compositions used in the process according to the invention, preferably the dye composition Cii), may comprise at least one liquid organic compound with a Hansen solubility parameter $\delta H$ of greater than 0 and less than 16 $MPa^{1/2}$.

In the context of the present invention, such a compound is also known as a hydrotropic compound.

For the purposes of the present invention, the term "hydrotropic compound" means a compound that is capable of increasing the solubility of hydrophobic compounds in aqueous phases.

Said liquid compounds more preferably have a Hansen solubility parameter $\delta H$ of between 5 and 15.8 $MPa^{1/2}$, even more preferentially between 8 and 15.8 $MPa^{1/2}$, and better still between 8 and 15 $MPa^{1/2}$.

These compounds are liquid at a temperature of 25° C. and at atmospheric pressure (760 mmHg; i.e. 1.013×10⁵ Pa).

The compound(s) with a Hansen solubility parameter value $\delta H$ as defined previously are, for example, described in the reference publication *Hansen solubility parameters: A User's Handbook* by Charles M. Hansen, CRC Press, 2000, pages 167 to 185, or in the publication *Handbook of Solubility Parameters and Other Cohesion Parameters*, CRC Press, pages 95 to 121 and pages 177 to 185.

This solubility parameter value $\delta H$ is associated with the formation of hydrogen bonds. It may be recalled that there are three major types of interaction in organic compounds: non-polar interactions, permanent dipole-dipole interactions and interactions of hydrogen bonding type, the latter forming the subject of the parameter defining the hydrotropic compound present in the composition used in accordance with the invention.

In particular, the book *Handbook of Solubility Parameters and Other Cohesion Parameters*, CRC Press, pages 95 to 121 and pages 177 to 185, gives the equation $\delta H = (\Sigma - ^2 U_h / V)^{1/2}$
in which $^2U_h$ (in J·mol⁻¹) describes the contributions of the functional group considered in the solubility parameters associated with the hydrogen bonds (values in Table 14, page 183), this parameter $^2U_h$ also being described in the book *The relation between surface tension and solubility parameter in liquids*, Bagda, E, Farbe Lack, 84, 212, 1978; and V is the volume of the molecule.

It should be noted that the solubility parameter value $\delta H$ is usually given for a temperature of 25° C. and at atmospheric pressure (760 mmHg, i.e. 1.013×10⁵ Pa).

In particular, the liquid organic compounds with a Hansen solubility parameter value $\delta H$ of greater than 0 and less than 16 $MPa^{1/2}$ are nonionic compounds.

Said liquid organic compound(s) with a Hansen solubility parameter value $\delta H$ of greater than 0 and less than 16 $MPa^{1/2}$ may be chosen from:
alcohol ethers, in particular $C_1$-$C_4$ ethers of $C_5$-$C_{10}$ alcohols, which are preferably saturated, linear or branched, optionally interrupted with one or more non-adjacent ether functions;
aliphatic esters of $C_1$-$C_4$ carboxylic acids and of $C_3$-$C_{10}$ monoalcohols or polyhydroxylated alcohols, interrupted with one or more non-adjacent ether functions;
aromatic ethers, in particular of $C_6$-$C_{10}$, of a $C_1$-$C_6$ alkyl optionally bearing a hydroxyl group,
($C_6$-$C_{10}$)aryl($C_0$-$C_6$) alkyl ethers, of a $C_1$-$C_6$ alkyl optionally bearing a hydroxyl group,
alkanols bearing an aryl substituent, preferably for which the aryl part is $C_6$-$C_{10}$, advantageously $C_6$, and the alkyl part of the alkanol is $C_1$-$C_4$, this alkyl part possibly ending or being interrupted with a heteroatom, advantageously oxygen or a hydroxyl group, preferably such as benzyl alcohol;
lactones preferably of formula (iii), and also mixtures thereof, with:

(iii)

in which R' represents a hydrogen, a linear or branched $C_1$-$C_8$ alkyl, a linear or branched $C_1$-$C_4$ hydroxyalkyl, n being equal to 1, 2 or 3, and preferably R' represents a hydrogen, a linear or branched $C_1$-$C_6$ alkyl or a linear or branched $C_1$-$C_2$ hydroxyalkyl.

A particularly advantageous example of lactones that may be mentioned is γ-butyrolactone.

Mention may also be made of certain liquid alkanols, for instance 1-pentanol.

Preferably, said liquid organic compound(s) with a Hansen solubility parameter value $\delta H$ of greater than 0 and less than 16 $MPa^{1/2}$ are chosen from alcohol ethers, aliphatic esters, aromatic ethers and alkanols bearing aryl substituents, and mixtures thereof.

Even more preferentially, said liquid organic compound(s) according to the invention are chosen from dipropylene glycol monomethyl ether acetate, dipropylene glycol methyl ether, dipropylene glycol mono-n-butyl ether (the INCI name of which is PPG-2 Butyl Ether), tripropylene glycol methyl ether, propylene glycol n-butyl ether, propylene glycol n-propyl ether, propylene glycol monomethyl ether, diethylene glycol monomethyl ether and monoethyl ether, 3-phenyl-1-propanol, 2-phenyl-1-propanol, benzyl alcohol, benzyloxyethanol and phenoxyethanol, and mixtures of these compounds.

The liquid organic compound(s) with a Hansen solubility parameter value δH of greater than 0 and less than 16 MPa$^{1/2}$ are even more preferentially chosen from alkanols bearing aryl substituents and even more preferentially benzyl alcohol.

When it is (they are) present, the liquid organic compound(s) with a Hansen solubility parameter value δH of greater than 0 and less than 16 MPa$^{1/2}$ preferably represent a total content ranging from 0.5% to 35% by weight, preferably from 0.5% to 20% by weight and better still from 0.5% to 10% by weight relative to the total weight of the dye composition Ci) and/or of composition Cii), preferably of composition Cii).

In one variant of the invention, composition Ci and composition Cii) each comprise one or more liquid organic compounds with a Hansen solubility parameter value δH of greater than 0 and less than 16 MPa$^{1/2}$.

In particular, the liquid organic compound with a Hansen solubility parameter value δH of greater than 0 and less than 16 MPa$^{1/2}$ is preferably chosen from alcohol ethers, aliphatic esters, aromatic ethers and alkanols bearing aryl substituents, and mixtures thereof.

Preferably, the liquid organic compound(s) with a Hansen solubility parameter value δH of greater than 0 and less than 16 MPa$^{1/2}$ represent a total content ranging from 0.1% to 35% by weight, preferably from 0.1% to 20% by weight and better still from 0.5% to 10% by weight relative to the total weight of composition Ci) and of composition Cii).

Preferably, the liquid organic compound(s) with a Hansen solubility parameter value δH of greater than 0 and less than 16 MPa$^{1/2}$ represent a total content ranging from 0.5% to 10% by weight relative to the total weight of composition Ci) and relative to the weight of composition Cii).

e) Chemical Oxidizing Agent(s)

According to a particular embodiment of the invention, the dyeing process of the invention also uses one or more chemical oxidizing agents.

This embodiment is particularly preferred in the case where the dye composition Cii) used in the process according to the invention comprises at least one additional dye chosen from oxidation dyes.

The term "chemical oxidizing agent" means an oxidizing agent other than atmospheric oxygen. More particularly, the dyeing process uses i) hydrogen peroxide; ii) urea peroxide; iii) polymeric complexes that can release hydrogen peroxide, such as polyvinylpyrrolidone/H$_2$O$_2$, provided in particular in the form of powders, and the other polymeric complexes described in U.S. Pat. Nos. 5,008,093, 3,376,110 and 5,183,901; iv) oxidases in the presence of an appropriate substrate (for example, glucose in the case of glucose oxidase or uric acid with uricase); v) metal peroxides which generate hydrogen peroxide in water, such as calcium peroxide or magnesium peroxide; vi) perborates; and/or vii) percarbonates.

According to a preferred embodiment of the invention, the composition comprises one or more chemical oxidizing agents chosen from i) urea peroxide; ii) polymeric complexes which can release hydrogen peroxide chosen from polyvinylpyrrolidone/H$_2$O$_2$; iii) oxidases; iv) perborates and v) percarbonates.

In particular, the dyeing process uses hydrogen peroxide.

Moreover, the composition(s) comprising hydrogen peroxide or a hydrogen peroxide generating system may also include various adjuvants conventionally used in compositions for dyeing keratin fibres as defined below.

According to a particular embodiment of the invention, the chemical oxidizing agent(s) used preferably represent from 0.01% to 12% by weight of chemical oxidizing agents (preferably of hydrogen peroxide) and preferably from 0.2% to 6% relative to the total weight of the composition(s) containing it or them, and even more preferentially from 0.2% to 3% by weight.

When the process according to the invention uses at least one chemical oxidizing agent, it may be used by extemporaneous addition to one of the compositions, preferably to the dye composition Cii), just before applying said composition to the keratin fibres, or, independently, into a third composition not comprising any dye during an additional oxidation step.

According to another embodiment, the process according to the invention does not use any chemical oxidizing agent.

According to a particular embodiment of the invention, the process according to the invention does not use any hydrogen peroxide. Preferably, according to this embodiment, the process according to the invention does not use any chemical oxidizing agent.

f) Basifying Agent(s)

According to a particular embodiment of the invention, the dyeing process may use one or more basifying agents f). In this embodiment, preferably, the basifying agent(s) e) are in the dye composition with the dye(s) c) as defined previously.

The term "basifying agents" means that the bases as defined for e) may be mineral or organic. In particular, the bases are alkali metal hydroxides, such as sodium hydroxide, which results in sodium salts.

These basifying agents are bases that can increase the pH of the composition(s) in which they are present. The basifying agent is a Brønsted, Lowry or Lewis base. It may be mineral or organic.

Particularly, said agent is chosen from i) (bi)carbonates, ii) aqueous ammonia, iii) alkanolamines such as monoethanolamine, diethanolamine, triethanolamine and derivatives thereof, iv) oxyethylenated and/or oxypropylenated ethylenediamines, v) mineral or organic hydroxides, vi) alkali metal silicates such as sodium metasilicates, vii), amino acids, preferably basic amino acids such as arginine, lysine, ornithine, citrulline and histidine, and viii) the compounds of formula (II) below:

(II)

in which formula (II), W is a divalent (C$_1$-C$_8$)alkylene radical optionally substituted with at least one hydroxyl group or at least one (C$_1$-C$_4$)alkyl radical and/or optionally interrupted with at least one heteroatom, such as oxygen or sulfur, or by an —N(R$_e$)— group; R$_a$, R$_b$, R$_c$, R$_d$ and R$_e$, which may be identical or different, represent a hydrogen atom or a (C$_1$-C$_4$)alkyl or hydroxy(C$_1$-C$_4$)alkyl radical; preferably, W represents a propylene radical. The mineral or organic hydroxides are preferably chosen from a) hydroxides of an alkali metal, b) hydroxides of an alkaline-earth metal, for instance sodium hydroxide or potassium hydroxide, c) hydroxides of a transition metal, such as hydroxides of metals from groups III, IV, V and VI, d) hydroxides of lanthanides or actinides, quaternary ammonium hydroxides and guanidinium hydroxide.

The hydroxide may be formed in situ, for instance guanidine hydroxide, formed by reacting calcium hydroxide with guanidine carbonate.

The term "(bi)carbonates" i) is understood to mean:

a) carbonates of alkali metals ($Met_2^+$, $CO_3^{2-}$), of alkaline-earth metals ($Met'^{2+}$, $CO_3^{2-}$) of ammonium (($R''_4N^+)_2,CO_3^{2-}$) or of phosphonium (($R''_4P^+)_2,CO_3^{2-}$ with Met' representing an alkaline-earth metal and Met representing an alkali metal, and R", which may be identical or different, represent a hydrogen atom or an optionally substituted ($C_1$-$C_6$)alkyl group such as hydroxyethyl), and b) bicarbonates, also known as hydrogen carbonates, of the following formulae:

$R'^+$, $HCO_3^-$, with R' representing a hydrogen atom, an alkali metal, an ammonium group $R''_4N^+$— or a phosphonium group $R''_4P^+$—, where R", which may be identical or different, represent a hydrogen atom or an optionally substituted ($C_1$-$C_6$)alkyl group, such as hydroxyethyl, and, when R' represents a hydrogen atom, the hydrogen carbonate is then known as dihydrogen carbonate ($CO_2$, $H_2O$); and $Met'^{2+}$ $(HCO_3^-)_2$, with Met' representing an alkaline-earth metal.

More particularly, the basifying agent is chosen from alkali metal or alkaline-earth metal (bi)carbonates and amino acids such as arginine; preferentially alkali metal (bi)carbonates and amino acids.

Mention may be made of Na, K, Mg and Ca carbonates or hydrogen carbonates and mixtures thereof, and in particular Na hydrogen carbonate. These hydrogen carbonates may originate from a natural water, for example spring water from the Vichy basin or from La Roche Posay or Badoit water (cf. for example, patent FR 2 814 943). Mention may in particular be made of sodium carbonate [497-19-8]= $Na_2CO_3$, sodium hydrogen carbonate or sodium bicarbonate [144-55-8]=$NaHCO_3$, and sodium dihydrogen carbonate=$Na(HCO_3)_2$.

According to a particularly advantageous embodiment, the basifying agent(s) e) are chosen from aqueous ammonia and alkanolamines such as monoethanolamine, preferably aqueous ammonia.

According to a particularly advantageous embodiment, the basifying agent(s) e) are chosen from aqueous ammonia, carbonates, bicarbonates and arginine, and mixtures thereof.

The basifying agent(s) as defined previously preferably represent from 0.001% to 10% by weight relative to the weight of the composition(s) containing them, and more particularly from 0.005% to 8% by weight of the composition.

The Compositions:

The compositions used in the process according to the invention generally comprise water or a mixture of water and of one or more organic solvents or a mixture of organic solvents.

The term "organic solvent" means an organic substance that is capable of dissolving or dispersing another substance without chemically modifying it.

Additional Organic Solvents:

As additional organic solvent (other than the liquid organic compound(s) with a Hansen solubility parameter value δH of greater than 0 and less than 16 $MPa^{1/2}$ mentioned previously), examples that may be mentioned include $C_1$-$C_4$ lower alkanols, such as ethanol and isopropanol; polyols and polyol ethers.

Preferably, composition Ci) and/or the dye composition Cii) comprises at least one $C_1$-$C_4$ lower alkanol, such as ethanol and isopropanol.

Preferably, composition Ci) and/or the dye composition Cii) comprises ethanol.

The additional organic solvents (other than the liquid organic compound(s) with a Hansen solubility parameter value δH of greater than 0 and less than 16 $MPa^{1/2}$) may be present in a total content preferably between 1% and 40% by weight approximately relative to the total weight of the dye composition Cii), and even more preferentially between 5% and 30% by weight approximately.

The Adjuvants:

The compositions of the dyeing process in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

Said adjuvants are preferably chosen from surfactants such as anionic or nonionic surfactants or mixtures thereof and mineral or organic thickeners.

The above adjuvants are generally present in an amount for each of them of between 0.01% and 40% by weight relative to the weight of the composition, and preferably between 0.1% and 20% by weight relative to the weight of the composition.

Needless to say, a person skilled in the art will take care to select this or these additional compound(s) such that the advantageous properties intrinsically associated with the composition(s) that are useful in the dyeing process in accordance with the invention are not, or are not substantially, adversely affected by the envisaged addition(s).

The cosmetic composition(s) used according to the process of the invention may be in various galenical forms, such as a powder, a lotion, a mousse, a cream or a gel, or in any other form that is suitable for dyeing keratin fibres. They may also be packaged in a propellant-free pump-action bottle or under pressure in an aerosol container in the presence of a propellant and form a foam.

pH of the Compositions

Preferably, the pH of at least one of the cosmetic compositions comprising at least one of the ingredients a) to e) is acidic, i.e. it has a pH of less than 7.0, preferably less than 5.0, in particular at a pH of between 0 and 4 inclusive, more particularly between 0.5 and 3.5, preferably between 1 and 3. Preferably, composition Ci) is acidic (i.e. it has a pH of less than 7.0), preferably has a pH of less than 5.0, particularly at a pH of between 0 and 4, more particularly between 0.5 and 3.5 and preferably between 1 and 3.

According to one embodiment, the pH of the cosmetic composition(s) comprising one or more alkaline agents is alkaline, is greater than 7, preferably between 8 and 12 and more particularly between 8 and 11 inclusive.

According to a particular embodiment of the invention, composition i) containing the titanium salt(s) a) and not containing any basifying agent e) has a pH of less than 7 and preferably of less than 5, in particular a pH between 0 and 4.

The pH of these compositions may be adjusted to the desired value by means of basifying agents as defined previously in f) or by using acidifying agents usually used in the dyeing of keratin fibres, or alternatively by means of standard buffer systems. Among the acidifying agents for the compositions used in the invention, examples that may be mentioned include mineral or organic acids, for instance hydrochloric acid, orthophosphoric acid, sulfuric acid, and carboxylic acids, for instance acetic acid.

Multi-Step Dyeing Process

The process for dyeing keratin fibres of the invention uses
i) at least one step of treating with a composition Ci) as defined previously,
ii) at least one step of dyeing with a dye composition Cii) as defined previously,
iii) and optionally at least one intermediate rinsing step, said step being performed between step i) and ii) or between step ii) and i), depending on the order in which said steps i) and ii) are performed.

Thus, the process according to the invention uses at least two steps that are different from each other: at least one treating step i) and at least one dyeing step ii).

According to a first embodiment of the invention, step i) of treating with composition Ci) is performed after step ii) of dyeing with composition Cii).

According to a second preferred embodiment of the invention, step i) of treating with composition Ci) is performed before step ii) of dyeing with composition Cii).

Preferably, according to one or other of these embodiments, the process according to the invention uses an intermediate rinsing step.

Thus, the intermediate rinsing step iii) is performed between step i) of treating with composition (Ci) and step ii) of dyeing with composition (Cii), or between step ii) of dyeing with composition Cii) and step i) of treating with composition Ci).

Intermediate Rinsing Step

According to a preferred embodiment of the invention, the process according to the invention may comprise an intermediate rinsing step iii).

According to this embodiment, said rinsing step is performed between step i) and ii) or between step ii) and i), depending on the order in which said steps i) and ii) are performed.

Particularly preferably, when the intermediate rinsing step iii) is present, it is performed with a composition comprising water. In particular, according to a preferred embodiment of the invention, said intermediate rinsing step iii) is performed exclusively with water, without adding an additional compound. According to another embodiment, the composition used for performing the rinsing step may also comprise one or more additional compounds.

This means that, according to a first particular embodiment of the invention, the process according to the invention comprises the implementation of a step of pretreating keratin fibres via the application thereto of a composition Ci), preferably followed by a step of rinsing these fibres, preferably with water, followed by performing a dyeing step via the application of a dye composition Cii) to the fibres, in which:

the cosmetic composition Ci) comprises a) one or more titanium salts; in particular, preferably, the titanium atom of said salt(s) is of oxidation state 2, 3 or 4, denoted Ti(II), Ti(III) or Ti(IV), preferably Ti(IV); and
b) optionally one or more carboxylic acids of formula (I); and the cosmetic composition Cii) comprises c) one or more dyes chosen from synthetic direct dyes, preferably chosen from anionic synthetic dyes.

In other words, according to this embodiment, the dyeing process according to the invention uses a step of pretreating with composition Ci) preferably followed by a step of rinsing the fibres before the step of the dyeing with composition Cii).

According to a second embodiment of the invention, the process according to the invention comprises the implementation of a step of treating keratin fibres via the application thereto of a dye composition Cii), followed by a step of rinsing these fibres, preferably with water, followed by performing a post-treatment step via the application of a composition Ci) to the fibres, in which:
the cosmetic composition Ci) comprises a) one or more titanium salts; in particular, preferably, the titanium atom of said salt(s) is of oxidation state 2, 3 or 4, denoted Ti(II), Ti(III) or Ti(IV), preferably Ti(IV); and
b) optionally one or more carboxylic acids of formula (I); and the cosmetic composition Cii) comprises c) one or more dyes chosen from synthetic direct dyes, preferably chosen from anionic synthetic dyes.

According to a particular embodiment, composition Ci) of the dyeing process of the invention also comprises b) one or more carboxylic acids of formula (I) below or a salt thereof;

in which formula (I):
A represents a saturated or unsaturated, cyclic or non-cyclic and aromatic or non-aromatic hydrocarbon-based group, which is monovalent when n has the value zero or polyvalent when n is greater than or equal to 1, comprising from 1 to 50 carbon atoms, which is optionally interrupted with one or more heteroatoms and/or optionally substituted, especially with one or more hydroxyl groups; preferably, A represents a monovalent ($C_1$-$C_6$)alkyl group or a polyvalent ($C_1$-$C_6$)alkylene group optionally substituted with one or more hydroxyl groups;
n represents an integer between 0 and 10 inclusive; preferably, n is between 0 and 5, such as between 0 and 2.

Preferentially, the organic titanium salt(s) of composition Ci) of the process of the invention are chosen from those of formulae (I-A), (I-B) or the salts of dihydroxybis(lactato) titaniumIV as defined previously.

According to a preferred embodiment of the invention, the dyeing process involves the application to said fibres of composition Ci) as defined previously, followed by rinsing said fibres, preferably with water, followed by the application to said fibres of composition Cii) as defined previously.

In particular, in the dyeing process of the invention, the leave-on time of composition Ci) as defined previously on the keratin fibres is between 5 minutes and 2 hours, more particularly between 15 minutes and 1 hour, preferably between 30 and 45 minutes. Preferentially, the leave-on time of composition Ci) on the keratin fibres is performed at a temperature of between 20° C. and 50° C., more preferentially between room temperature (27° C.) and 40° C.

Between the application of compositions i) and ii) or ii) and i), at least one rinsing step is performed in the process of the invention.

According to a particular embodiment, composition Cii) of the dyeing process of the invention also comprises one or more chemical oxidizing agents chosen especially from hydrogen peroxide and one or more hydrogen peroxide-generating systems as defined previously.

Preferably, composition Cii) of the dyeing process of the invention also comprises one or more chemical oxidizing agents when said composition also comprises at least one oxidation dye as additional dye.

When composition Cii) comprises an oxidation dye as additional dye and at least one chemical oxidizing agent, it is also known as a "ready-to-use" oxidation dye composition. This ready-to-use dye composition is preferably prepared a few minutes before application, in particular between 1 minute and 20 minutes, more particularly between 5 minutes and 10 minutes before application. The ready-to-use composition is prepared by uniformly mixing the dye composition comprising c) at least one synthetic direct dye and at least one oxidation base as defined previously and optionally at least one coupler as defined previously, with an oxidizing composition e) comprising at least one chemical oxidizing agent as defined previously.

Once the ready-to-use dye composition has been prepared, it is preferably applied immediately to the keratin fibres. The leave-on time of composition Cii), in particular of the ready-to-use dye composition, on the keratin fibres is between 1 minute and 2 hours, preferably between 5 minutes and 1 hour; the leave-on time is more preferentially from 15 to 30 minutes. Preferentially, the leave-on time of composition Cii) on the keratin fibres is performed at a temperature of between 20° C. and 50° C., preferentially between room temperature (27° C.) and 40° C.

Preferably, at least one of the compositions used in the dyeing process is at acidic pH, i.e. less than 7.0, preferably less than 5, in particular at a pH of between 0 and 4 inclusive, more particularly between 0.5 and 3.5 and more preferentially between 1 and 3. In particular, composition Ci) according to the invention is at acidic pH, preferably less than 5, in particular at a pH of between 0 and 4 inclusive, more particularly between 0.5 and 3.5 and more preferentially between 1 and 3.

Preferably, the compositions used in the process of the invention are aqueous.

According to a particular embodiment of the invention, the dye composition Cii) comprising the synthetic direct dye(s) as defined previously and optionally at least one additional oxidation dye also comprises one or more basifying agents f) as defined previously, preferably aqueous ammonia. In particular, the pH of the composition comprising one or more basifying agents, preferably composition ii), is between 8 and 12, particularly between 8 and 11.

After applying the compositions Ci), optionally rinsing the keratin fibres and applying composition Cii), and vice versa, the dyeing process of the invention may involve one or more shampoo washes, followed by one or more rinses of the keratin fibres with water, optionally followed by drying via a heat treatment by heating to a temperature of between 30 and 60° C. In practice, this operation may be performed using a styling hood, a hairdryer, an infrared ray dispenser and other standard heating appliances.

Use may also be made, as a means for both heating and for straightening the head of hair, of a heating iron at a temperature of between 600° C. and 220° C. and preferably between 120° C. and 200° C.

The term "drying" means the action of evaporating the organic solvents and/or water present in one or more compositions used in the process of the invention, comprising or not comprising one or more ingredients a) to e) as defined previously. The drying may be performed with a source of heat (convection, conduction or radiation) by sending, for example, a stream of hot gas such as air necessary to evaporate the solvent(s). Sources of heat that may be mentioned include a hairdryer, a hairstyling hood, a hair-straightening iron, an infrared ray dispenser or other standard heating appliances.

One particular mode of the invention relates to a dyeing process that is performed at room temperature (25° C.).

In all the particular forms and variants of the processes previously described, the compositions mentioned are ready-to-use compositions that may result from the extemporaneous mixing of two or more compositions and in particular of compositions present in dyeing kits.

The examples that follow serve to illustrate the invention without, however, being limiting in nature.

EXAMPLE 1

The following compositions were prepared from the following ingredients in the following proportions, indicated in grams per 100 grams of composition:

Pretreatment Composition Ci):

| Ingredients | Composition Ci) 1 (% in g) |
|---|---|
| Glycolic acid | 15 g |
| Dihydroxybis(ammonium lactato)titanium(IV) at 50% by weight | 10.3 g |
| Water | qs 100 g |
| pH agent | qs pH = 2 ± 0.3 |

Dye Composition Cii):

| Ingredients | Composition Cii) 2 (% in g) |
|---|---|
| Carmine indigo Indigotine at 85% sold by LCW Sensient | 4 g |
| Ethanol | 24 g |
| Benzyl alcohol | 10 g |
| Water | qs 100 g |
| pH agent | qs pH = 2 ± 0.3 |

Protocol

The study relates to locks of natural Caucasian hair containing 90% white hairs (90 NW).

According to a first treatment process P1 according to the invention, these various locks are pretreated with composition Ci) comprising the titanium salt in a proportion of 3.33 g of composition per gram of hair. During this pretreatment step, composition Ci) is left to stand for 45 minutes on a lock at 40° C., and the lock is then rinsed with running tap water and drained dry. The dye composition Cii) is then applied to the lock in a proportion of 3.33 g of composition per gram of hair and left to stand for 45 minutes at 40° C.

In parallel, according to a second comparative treatment process P2 outside the invention, the lock is not pretreated with composition Ci), but is only moistened. The dye composition Cii) is then applied to the lock in a proportion of 3.33 g of composition per gram of hair and left to stand for 45 minutes at 40° C.

After these leave-on times, the lock is washed with Elvive multivitamin shampoo, rinsed and then dried under a hood.

Dyeing Results

With the locks of hair dyed according to the process of the invention, i.e. with pretreatment with the titanium salts, very intensely dyed locks were obtained, whereas those which did not receive the titanium pretreatment are weakly dyed. These results are confirmed with the L, a and b spectrophotometer measurements.

The colorimetric measurements were performed using a Minolta CM3600D spectrocolorimeter (illuminant D65, angle 10°, specular component included) in the CIELab system.

In this system, L* represents the lightness. The smaller the value of L*, the darker and more powerful the colouring obtained.

The colour build-up is represented by the colour difference $\Delta E$ between the non-dyed lock and the dyed lock: the greater the value of $\Delta E$, the greater the colour build-up. This value is calculated from the following equation (i):

$$\Delta E = \sqrt{(L^* - L_0^*)^2 + (a^* - a_0^*)^2 + (b^* - b_0^*)^2} \quad (i)$$

In this equation, $L^*$, $a^*$ and $b^*$ represent the values measured on undyed locks of hair and $L_0^*$, $a_0^*$ and $b_0^*$ represent the values measured on dyed locks of hair.

The results L and $\Delta L$ of colour build-up are collated in the table below:

Intense blueish-black colourings were obtained, as shown by the colorimetric measurements:

| Process | Hair | L* | a* | b* | $\Delta E^*$ build-up | Colour |
|---|---|---|---|---|---|---|
| Comparative process without pretreatment with titanium salt: treatment directly with the dye composition 2 | NW | 55.25 | −12.41 | 0.19 | 21.87 | Sky-blue |
| Process according to the invention with pretreatment with titanium salt (composition 1 followed by rinsing and then application of composition 2) | NW | 25.34 | −5.97 | −15.44 | 49.32 | Deep blue |

It is clearly seen that the lock dyed according to the process of the invention with composition Ci) 1 and then rinsed with the dye composition Cii) 2 is dyed much more intensely and with significantly greater colour build-up than that obtained with the lock dyed according to the comparative process without pretreatment with the composition comprising the titanium salt, since the value of L decreases greatly according to the invention and the value of the colour build-up $\Delta E$ is higher according to the invention.

EXAMPLE 2

The following compositions were prepared from the following ingredients in the following proportions, indicated in grams per 100 grams of composition:

Pretreatment composition C(i): identical to that of Example 1 (composition 1 Ci))

| Ingredients | Composition Ci) 1 (% in g) |
|---|---|
| Glycolic acid | 15 g |
| Dihydroxybis(ammonium lactato) titanium(IV) at 50% by weight | 10.3 g |
| Water | qs 100 g |
| pH agent | qs pH = 2 ± 0.3 |

Dye composition C(ii): the three dye compositions C3, C4 and C5 below each comprising a different anionic direct dye were prepared:

| Ingredients | Composition Cii) 3 (% in g) | Composition Cii) 4 (% in g) | Composition Cii) 5 (% in g) |
|---|---|---|---|
| Acid Black 1 | 0.1 | — | — |
| Acid Blue 62 | — | 0.1 | — |
| Acid Red 18 | — | — | 0.1 g |
| Ethanol | 15 | 15 | 15 |
| Benzyl alcohol | 5 | 5 | 5 |
| Water | qs 100 g | qs 100 g | qs 100 g |
| pH | pH 7 | pH 7 | pH 7 |

Protocol

The study relates to locks of natural Caucasian hair containing 90% white hairs (90 NW).

According to a first dyeing process P1 according to the invention, three locks are pretreated with composition Ci) 1 comprising the titanium salt in a proportion of 3.33 g of composition per gram of hair. During this pretreatment step, composition Ci) is left to stand for 15 minutes on each lock at 40° C., and each lock is then rinsed with running tap water and drained dry. Each of the dye compositions Cii) 3, 4 and 5 is then applied separately to each of the three locks in a proportion of 3.33 g of composition per gram of hair and left to stand for 15 minutes at 40° C.

In parallel, according to a second comparative treatment process P2 outside the invention, the three different locks are not pretreated with composition Ci) 1, but are preferably moistened. The dye compositions Cii) 3, 4 and 5 are then separately applied to each of the three locks in a proportion of 3.33 g of composition per gram of hair and left to stand for 15 minutes at 40° C. According to this dyeing process, there is therefore no step of pretreating the locks with composition Ci) 1.

The following results are obtained according to the same evaluation protocol as that used in the preceding example.

| Acidic dye | Process | L* | a* | b* | ΔE* build-up | Colour |
|---|---|---|---|---|---|---|
| Acid Black 1 | Comparative process without pretreatment with titanium salt (application of composition 3 comprising Acid Black 1) | 52.18 | −6.59 | 4.61 | 15.8 | Light blue-green |
| | Process according to the invention with pretreatment with titanium salt (composition 1 followed by rinsing and then application of composition 3 comprising Acid Black 1) | 25.03 | −7.1 | −8.01 | 44.08 | Blue |
| Acid Blue 62 | Comparative process without pretreatment with titanium salt (application of composition 4 comprising Acid Blue 62) | 57.28 | −5.65 | 4.66 | 14.2 | Light blue |
| | Process according to the invention with pretreatment with titanium salt (composition 1 followed by rinsing and then application of composition 4 comprising Acid Blue 62) | 37.82 | −8.31 | −19.41 | 44.6 | Deep blue |
| Acid Red 18 | Comparative process without pretreatment with titanium salt (application of composition 5 comprising Acid Red 18) | 66.79 | 3.03 | 14.56 | 2.8 | Pink-beige |
| | Process according to the invention with pretreatment with titanium salt (composition 1 followed by rinsing and then application of composition 5 comprising Acid Red 18) | 44.2 | 37.7 | 14.02 | 42.7 | Red |

It is clearly seen that the locks dyed according to the process of the invention with composition Ci) 1 and then rinsed with the dye compositions Cii) 3, 4 or 5 are dyed much more intensely and with significantly greater colour build-up than that obtained with the locks dyed according to the comparative process without pretreatment with composition Ci) 1 comprising the titanium salt, since the value of L decreases greatly according to the invention and the value of the colour build-up ΔE is higher according to the invention.

The invention claimed is:

1. A method for dyeing keratin fibers, comprising:
    i) treating the fibers using a cosmetic composition Ci), the cosmetic composition Ci) comprising:
        a) at least one titanium salt, wherein the at least one titanium salt is chosen from those according to formula (I-A) below:

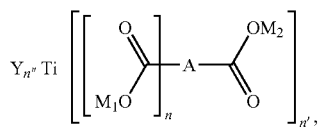

wherein:
    A is chosen from a monovalent group when n has the value zero, or a polyvalent group when n is greater than or equal to 1, saturated or unsaturated, cyclic or non-cyclic and aromatic or non-aromatic hydrocarbon-based group comprising from 1 to 50 carbon atoms which is optionally interrupted with at least one heteroatom and/or optionally substituted;
    n, n', and n" may be identical or different, n is an integer ranging from 0 to 4, n' and n" are equal to 1, 2, 3, or 4, and n'+n" is equal to 6;
    $M_1$ and $M_2$, which may be identical or different, are chosen from cationic counterions; and
    $TiY_{n''}$ is chosen from $Ti(OH)_{n''}$, or $Ti(O)_{n''/2}$, or $Ti(OH)_{m1}(O)_{m2}$, wherein m1+m2 is equal to n";
        b) at least one carboxylic acid according to formula (I) below or a salt thereof:

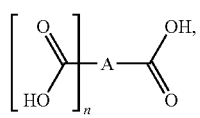

wherein:
    A is chosen from a monovalent ($C_1$-$C_6$)alkyl group or a polyvalent ($C_1$-$C_6$)alkylene group optionally substituted with one or more hydroxyl and/or amino groups;
    n is an integer ranging from 0 to 10;
    ii) dyeing the fibers with a coloring cosmetic composition Cii), the coloring cosmetic composition Cii) comprising at least one synthetic direct dye; and
    iii) optionally, rinsing the fibers.

2. The method according to claim 1, wherein A is chosen from a monovalent ($C_1$-$C_6$)alkyl or polyvalent ($C_1$-$C_6$)alkylene group optionally substituted with at least one hydroxyl group or at least one amino group.

3. The method according to claim 1, wherein the at least one titanium salt is chosen from those according to formula (I-B) below:

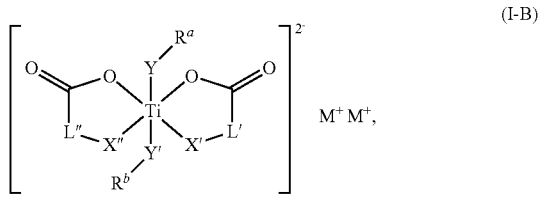

wherein:
- L' and L", which may be identical or different, are chosen from a divalent (hetero)arylene, $(C_1-C_6)$alkylene, or $(C_2-C_6)$alkenylene group, optionally substituted with at least one atom or group chosen from halo, $(C_1-C_4)$alkyl, hydroxyl, thiol, $(di)(C_1-C_4)$(alkyl)amino, carboxyl, and/or optionally interrupted with at least one heteroatom;
- X' and X", which may be identical or different, are chosen from heteroatoms, a hydrogen atom, or a $(C_1-C_4)$alkyl group;
- Y and Y', which may be identical or different, are chosen from heteroatoms;
- $R^a$ and $R^b$, which may be identical or different, are chosen from a hydrogen atom, $(C_1-C_6)$alkyl group, $(C_2-C_6)$alkenyl group, or (hetero)aryl group;
- $M^+$, which may be identical or different, is chosen from cationic counterions.

4. The method according to claim 1, wherein the at least one titanium salt is chosen from salts of dihydroxybis(lactato)titaniumIV.

5. The method according to claim 4, wherein the at least one titanium salt is chosen from salts of dihydroxybis(lactato)titaniumIV according to the following formula:

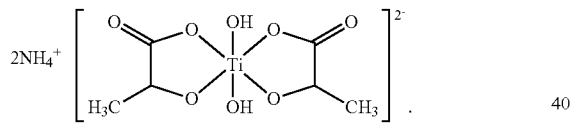

6. The method according to claim 1, wherein the at least one titanium salt is chosen from inorganic salts of Ti(II), Ti(III), or Ti(IV).

7. The method according to claim 1, wherein the at least one titanium salt is present in cosmetic composition Ci) in an amount ranging from about 0.001% to about 20% by weight, relative to the total weight of cosmetic composition Ci).

8. The method according to claim 1, wherein the at least one synthetic direct dye is chosen from anionic direct dyes, acidic azo dyes, acidic azine dyes, acidic triarylmethane dyes, acidic indoamine dyes, acidic anthraquinone dyes, or acidic indigoids, wherein the dyes comprise at least one sulfonate or carboxylate group bearing a cationic counterion.

9. The method according to claim 8, wherein the anionic direct dyes are chosen from those according to formula (VI) below:

wherein:
- $Col^{(-)}{}_m$ is the anionic part of the anionic direct dye comprising in its structure at least one sulfonate group and/or at least one carboxylate group and comprising m anionic charges;
- m and n, which may be identical or different, are an integer ranging from 1 to 10;
- $Q^+$, which may be identical or different, is chosen from organic or mineral cationic counterions.

10. The method according to claim 8, wherein the anionic direct dyes are chosen from dyes according to formulae (VII), (VII'), (VIII), (VIII'), (IX), (IX'), (X), (X'), (XI), (XII), (XIII), and (XIV) below:

a) anionic diaryl azo dyes of formula (VII) or (VII'):

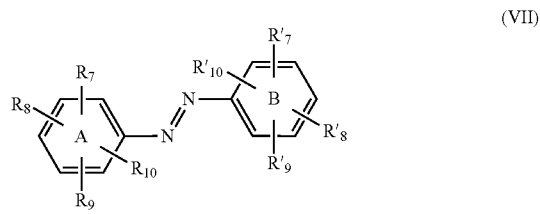

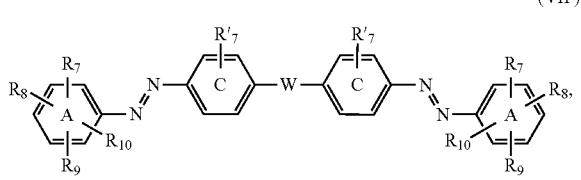

wherein:
- $R_7$, $R_8$, $R_9$, $R_{10}$, $R'_7$, $R'_8$, $R'_9$, and $R'_{10}$, which may be identical or different, are chosen from a hydrogen atom or a group chosen from: i) alkyl; ii) alkoxy; iii) alkylthio; iv) hydroxyl; v) mercapto; vi) nitro; vii) $R°—C(X)—X'—$, $R°—X'—C(X)—$, $R°—X'—C(X)—X"—$, wherein $R°$ is chosen from a hydrogen atom or an alkyl or aryl group, X, X', and X", which may be identical or different, are chosen from an oxygen or sulfur atom or NR, wherein R is chosen from a hydrogen atom or an alkyl group; viii) $(O)_2S(O^-)—$, $M^+$, wherein $M^+$ is a cationic counterion; ix) $(O)COO^-—$, $M^+$, wherein $M^+$ is a cationic counterion; x) $R"—S(O)_2—$, wherein $R"$ is chosen from a hydrogen atom, an alkyl group, an aryl group, a (di)(alkyl)amino group, or aryl(alkyl)amino group; xi) $R'''—S(O)_2—X'—$, wherein $R'''$ is chosen from an optionally substituted alkyl or aryl group, and X' is chosen from an oxygen or sulfur atom or NR, wherein R is chosen from a hydrogen atom or an alkyl group; xii) (di)(alkyl)amino; xiii) aryl(alkyl)amino optionally substituted with at least one group chosen from nitro, nitroso, or $(O)_2S(O^-)—$, $M^+$ and alkoxy, wherein $M^+$ is a cationic counterion; xiv) optionally substituted heteroaryl; xv) cycloalkyl; or xvi) Ar—N=N—, wherein Ar is an optionally substituted aryl group;
- or alternatively, two contiguous groups $R_7$ with $R_8$ or $R_8$ with $R_9$ or $R_9$ with $R_{10}$ together form a fused benzo group A'; and $R'_7$ with $R'_8$ or $R'_8$ with $R'_9$ or $R'_9$ with $R'_{10}$ together form a fused benzo group B'; with A' and B' optionally substituted with at least one group chosen from i) nitro; ii) nitroso; iii) $(O)_2S(O^-)—$, $M^+$; iv) hydroxyl; v) mercapto; vi) (di)(alkyl)amino; vii) $R°—C(X)—X'—$; viii) $R°—X'—C(X)—$; ix) $R°—X'—C(X)—X"—$; x) Ar—N=N; or xi) optionally substituted aryl(alkyl)amino; and
- W represents a sigma bond σ, an oxygen or sulfur atom, or a divalent radical i) —N(R)— wherein R is chosen from a hydrogen atom or an alkyl group, or
ii) methylene —C(R$_a$)(R$_b$)—, wherein R$_a$ and R$_b$, which may be identical or different, are chosen from a hydrogen atom or an aryl group, or alternatively R$_a$ and R$_b$ form, together with the carbon atom that bears them, a spiro cycloalkyl;

wherein formulae (VII) and (VII') comprise at least one sulfonate
(O)$_2$S(O$^-$)—, Q$^+$ or carboxylate (O)C(O$^-$)—, Q$^+$ radical on one of the rings A, A', B, B' or C with R$_1$R$_2$R$_3$R$_4$ as defined previously;

c3b) pyrazolone anionic azo dyes of formulae (VIII) and (VIII'):

Y is chosen from a hydroxyl group or an oxo group; and

- - - - represents a single bond when Y is an oxo group; and represents a double bond when Y represents a hydroxyl group;

further wherein formulae (VIII) and (VIII') comprise at least one sulfonate group (O)$_2$S(O$^-$)—, Q$^+$ on one of the rings D or E or formulae (VIII) and (VIII') comprise at least one carboxylate group (O)C(O$^-$)—, Q$^+$, wherein Q$^+$ is chosen from organic or mineral cationic counterions;

c3c) anthraquinone dyes of formulae (IX) and (IX'):

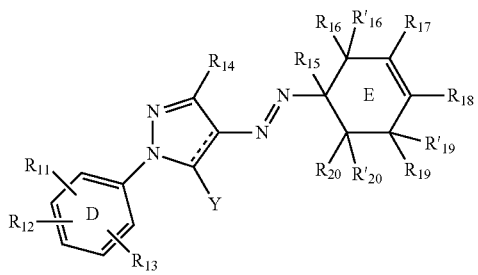

(VIII)

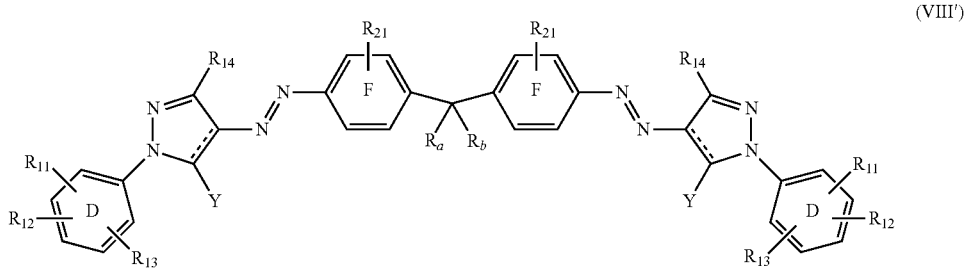

(VIII')

wherein;
R$_{11}$, R$_{12}$, and R$_{13}$, which may be identical or different, are chosen from a hydrogen atom, halogen atom, alkyl group, or —(O)$_2$S(O$^-$), M$^+$ wherein M$^+$ is a cationic counterion;

R$_{14}$ is chosen from a hydrogen atom, alkyl group, or C(O)O$^-$, M$^+$ wherein M$^+$ is a cationic counterion;

R$_{15}$ is a hydrogen atom;

R$_{16}$ is chosen from an oxo group, wherein R'$_{16}$ is absent, or alternatively R$_{15}$ with R$_{16}$ together form a double bond;

R$_{17}$ and R$_{18}$, which may be identical or different, are chosen from a hydrogen atom or a group chosen from: (O)$_2$S(O$^-$)—, M$^+$ wherein M$^+$ is a cationic counterion; or
Ar—O—S(O)$_2$— with Ar representing an optionally substituted aryl group;

R$_{19}$ and R$_{20}$ together form either a double bond, or a benzo group D', which is optionally substituted;

R'$_{16}$, R'$_{19}$ and R'$_{20}$, which may be identical or different, are chosen from a hydrogen atom or an alkyl or hydroxyl group;

R$_{21}$ is chosen from a hydrogen atom or an alkyl or alkoxy group;

R$_a$ and R$_b$, which may be identical or different, are chosen from a hydrogen atom, or a (C$_1$-C$_6$)alkyl, (C$_2$-C$_6$) alkenyl, or (hetero)aryl group;

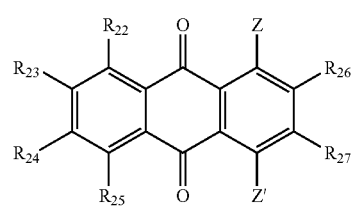

(IX)

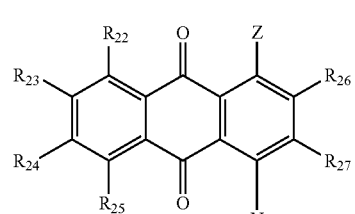

(IX')

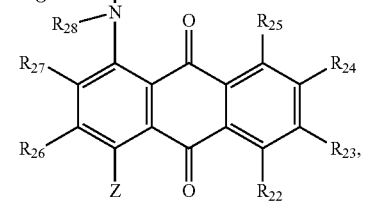

wherein:
R$_{22}$, R$_{23}$, R$_{24}$, R$_{25}$, R$_{26}$, and R$_{27}$, which may be identical or different, are chosen from a hydrogen atom, halogen atom, or a group chosen from i) alkyl, ii) hydroxyl, iii) mercapto, iv) alkoxy, v) alkylthio, vi) aryloxy or arylthio which is optionally substituted with at least one group chosen from alkyl and
(O)$_2$S(O$^-$)—, M$^+$, wherein M$^+$ is a cationic counterion, vii) aryl(alkyl)amino optionally substituted with at least one group chosen from alkyl and (O)$_2$S(O$^-$)—, M$^+$ wherein M$^+$ is a cationic counterion, viii) (di) (alkyl)amino, ix) (di)(hydroxyalkyl)amino, or x) (O)$_2$S (O$^-$)—, M$^+$, wherein M$^+$ is a cationic counterion;
Z' is chosen from a hydrogen atom or a NR$_{28}$R$_{29}$ group, wherein R$_{28}$ and R$_{29}$, which may be identical or different, are chosen from a hydrogen atom or a group chosen from i) alkyl, ii) polyhydroxyalkyl, iii) aryl optionally substituted with at least one group, or iv) cycloakyl; and
Z is chosen from hydroxyl or NR'28R'29, wherein R'28 and R'29, which may be identical or different, are chosen from a hydrogen atom or a group chosen from i) alkyl, ii) polyhydroxyalky, iii) aryl optionally substituted with at least one group, or iv) cycloakyl;
further wherein formulae (IX) and (IX') comprise at least one sulfonate group (O)$_2$S(O$^-$)—, Q$^+$;
c3d) nitro dyes of formulae (X) and (X'):

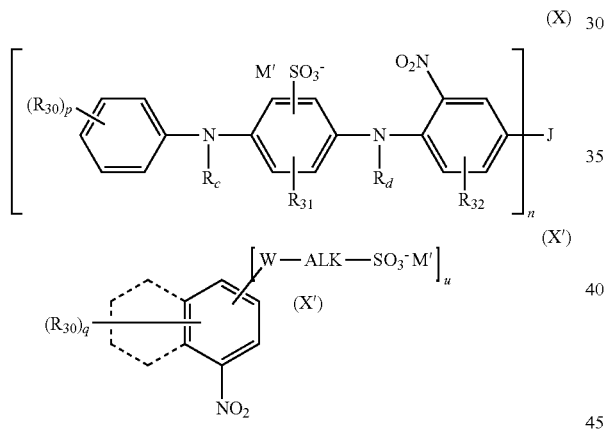

wherein:
R$_{30}$, R$_{31}$, and R$_{32}$, which may be identical or different, are chosen from a hydrogen atom, a halogen atom, or a group chosen from i) alkyl, ii) alkoxy optionally substituted with at least one hydroxyl group, iii) alkylthio optionally substituted with at least one hydroxyl group, iv) hydroxyl, mercapto, v) nitro, nitroso, vi) (poly) haloalkyl, vii) R°—C(X)—X'—, R°—X'—C(X)—, R°—X'—C(X)—X"— with R°; wherein X, X' and X" which may be identical or different, are chosen from an oxygen or sulfur atom or NR, wherein R is chosen from a hydrogen atom or an alkyl group, viii) (O)$_2$S(O$^-$)—, M$^+$, wherein M$^+$ is a cationic counterion, ix) (O)CO$^-$—, M$^+$, wherein M$^+$ is a cationic counterion, x) (di)(alkyl)amino, xi) (di)(hydroxyalkyl)amino, or xii) heterocycloalkyl;
R$_c$ and R$_d$, which may be identical or different, are chosen from a hydrogen atom or an alkyl group;
W represents a sigma bond σ, an oxygen or sulfur atom, or a divalent radical i) —N(R)—, wherein R is chosen from a hydrogen atom or an alkyl group, or ii) methylene —C(R$_a$)(R$_b$)— with R$_a$ and R$_b$, which may be identical or different, representing a hydrogen atom or an aryl group, or alternatively R$_a$ and R$_b$ form, together with the carbon atom that bears them, a spiro cycloalkyl;
ALK is a linear or branched divalent C$_1$-C$_6$ alkylene group;
n is equal to 1 or 2;
p is an integer ranging from 1 to 5;
q is an integer ranging from 1 to 4;
u is equal to 0 or 1;
when n is equal to 1, J is a nitro or nitroso group;
when n is equal to 2, J is an oxygen or sulfur atom, or a divalent radical —S(O)$_m$—, wherein m is an integer 1 or 2;
M' is a cationic counterion; and

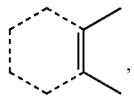

which may be present or absent, is a benzo group optionally substituted with at least one group R$_{30}$ chosen from a hydrogen atom, a halogen atom, or a group chosen from i) alkyl, ii) alkoxy optionally substituted with at least one hydroxyl group, iii) alkylthio optionally substituted with at least one hydroxyl group, iv) hydroxyl mercapto, v) nitro nitroso, vi) (poly) haloalkyl, vii) R°—C(X)—X'—, R°—X'—C(X)—, R°—X'—C(X)—X"— with R°; wherein X, X' and X" which may be identical or different, are chosen from an oxygen or sulfur atom or NR, wherein R is chosen from a hydrogen atom or an alkyl group, viii) (O)$_2$S(O$^-$)—, M$^+$ wherein M$^+$ is a cationic counterion, x) (O)CO$^-$—, M$^+$ wherein M$^+$ is a cationic counterion, xi) (di)(alkyl)amino, xii) (di)(hydroxyalkyl)amino, or xiii) heterocycloalkyl;
further wherein formulae (X) and (X') comprise at least one sulfonate group (O)$_2$S(O$^-$)—, Q$^+$ or carboxylate group (O)C(O$^-$)—, Q$^+$;
c3e) triarylmethane dyes of formula (XI):

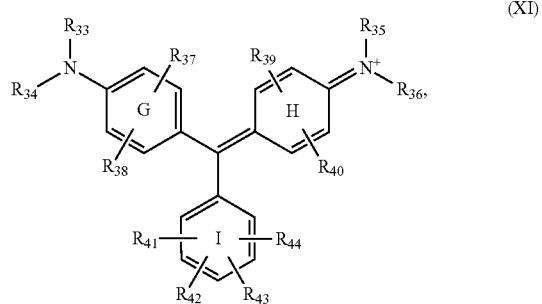

wherein:
R$_{33}$, R$_{34}$, R$_{35}$, and R$_{36}$, which may be identical or different, are chosen from a hydrogen atom or a group chosen from alkyl, optionally substituted aryl, or optionally substituted arylalkyl;
R$_{37}$, R$_{38}$, R$_{39}$, R$_{40}$, R$_{41}$, R$_{42}$, R$_{43}$, and R$_{44}$, which may be identical or different, are chosen from a hydrogen atom or a group chosen from: i) alkyl; ii) alkoxy; iii) alkylthio; iv) (di)(alkyl)amino; v) hydroxyl mercapto; vi) nitro nitroso; vii) R°—C(X)—X'—, R°—X'—C(X)—, or R°—X'—C(X)—X"—, wherein R° is chosen from a hydrogen atom or an alkyl or aryl group; X, X' and X", which may be identical or different, are chosen from an oxygen or sulfur atom or NR, wherein R is chosen from a hydrogen atom or an alkyl group; x) (O)$_2$S(O$^-$)—, M$^+$ wherein M$^+$ is chosen from a hydrogen atom or a cationic counterion; or viii) (O)CO$^-$—, M$^+$, wherein M$^+$ is chosen from a hydrogen atom or a cationic counterion;

or alternatively two contiguous groups $R_{41}$ with $R_{42}$ or $R_{42}$ with $R_{43}$ or $R_{43}$ with $R_{44}$ together form a fused benzo group: I'; with I' optionally substituted with at least one group chosen from i) nitro; ii) nitroso; iii) (O)$_2$S(O$^-$)—, M$^+$; iv) hydroxyl; v) mercapto; vi) (di)(alkyl)amino; vii) R°—C(X)—X'—; viii) R°—X'—C(X)—; or ix) R°—X'—C(X)—X"—; with M$^+$, R°, X, X' and X", wherein R° is chosen from a hydrogen atom or an alkyl or aryl group; X, X' and X", which may be identical or different, are chosen from an oxygen or sulfur atom or NR, wherein R is chosen from a hydrogen atom or an alkyl group;

c3f) xanthene-based dyes of formula (XII):

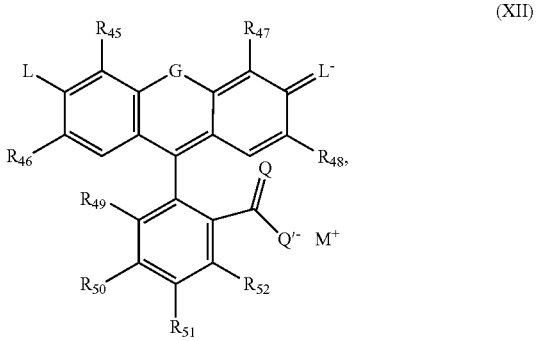

(XII)

wherein:
$R_{45}$, $R_{46}$, $R_{47}$, and $R_{48}$, which may be identical or different, are chosen from a hydrogen or halogen atom;
$R_{49}$, $R_{50}$, $R_{51}$, and $R_{52}$, which may be identical or different, are chosen from a hydrogen or halogen atom or a group chosen from i) alkyl; ii) alkoxy, alkylthio; iii) hydroxyl, mercapto; iv) nitro, nitroso; v) (O)$_2$S(O$^-$)—, M$^+$ with M$^+$ representing a hydrogen atom or a cationic counterion; or vi) (O)CO$^-$—, M$^+$, wherein M$^+$ is chosen from a hydrogen atom or a cationic counterion;
G is chosen from an oxygen or sulfur atom or a group NR$_e$, wherein R$_e$ is chosen from a hydrogen atom or a (C$_1$-C$_4$)alkyl group;
L is chosen from an alkoxide O$^-$, M$^+$; a thioalkoxide S$^-$, M$^+$ or a group NR$_f$, wherein R$_f$ is chosen from a hydrogen atom or an alkyl group and M$^+$ is chosen from a hydrogen atom or a cationic counterion;
L' is chosen from an oxygen or sulfur atom or an ammonium group: N+R$_f$R$_g$, wherein R$_f$ and R$_g$, which may be identical or different, are chosen from a hydrogen atom, an alkyl group or optionally substituted aryl;
Q and Q', which may be identical or different, are chosen from an oxygen or sulfur atom; and
M$^+$ is chosen from a hydrogen atom or a cationic counterion;

further wherein formula (XII) comprises at least one sulfonate group (O)$_2$S(O$^-$)—, Q$^+$ or carboxylate group (O)C(O$^-$)—, Q$^+$ wherein Q$^+$ is chosen from organic or mineral cationic counterions; or c3g) indigoid dyes of formula (XIII):

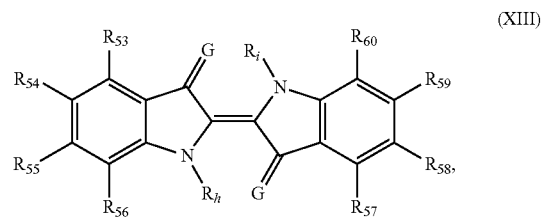

(XIII)

wherein:
$R_{53}$, $R_{54}$, $R_{55}$, $R_{56}$, $R_{57}$, $R_{58}$, $R_{59}$, and $R_{60}$, which may be identical or different, are chosen from a hydrogen atom or a group chosen from: i) alkyl; ii) alkoxy, alkylthio; iii) hydroxyl, mercapto; iv) nitro, nitroso; v) R°—C(X)—X'—, R°—X'—C(X)—, or R°—X'—C(X)—X"—, wherein R° is chosen from a hydrogen atom or an alkyl or aryl group; X, X' and X", which may be identical or different, are chosen from an oxygen or sulfur atom or NR, wherein R is chosen from a hydrogen atom or an alkyl group; vi) (O)$_2$S(O$^-$)—, M$^+$, wherein M$^+$ is chosen from organic or mineral cationic counterions; or vii) (O)CO$^-$—, M$^+$, wherein M$^+$ is chosen from organic or mineral cationic counterions;
G is chosen from an oxygen or sulfur atom or a group NR$_e$, wherein R$_e$ is chosen from hydrogen atom or a (C$_1$-C$_4$)alkyl group;
R$_i$ and R$_h$, which may be identical or different, are chosen from a hydrogen atom or an alkyl group;
wherein formula (XIII) comprises at least one sulfonate group (O)$_2$S(O$^-$)—, Q$^+$ or carboxylate group (O)C(O$^-$)—, Q$^+$, wherein Q$^+$ is chosen from organic or mineral cationic counterions.

11. The method according to claim 2, wherein the at least one synthetic direct dye is chosen from cationic and/or neutral direct dyes, azo direct dyes, quinone and anthraquinone direct dyes, azine, polyarylmethane, indoamine, polymethine, porphyrin, metalloporphyrin, phthalocyanine, or methine cyanine direct dyes.

12. The method according to claim 1, wherein the at least one carboxylic acid is present in an amount ranging from about 0.1% to about 20% by weight, relative to the total weight of the cosmetic composition Ci).

13. The method according to claim 1, wherein the cosmetic composition Ci) is acidic, and has a pH of less than about 5.0.

14. The method according to claim 1, further comprising using at least one liquid organic compound with a Hansen solubility parameter value δH of greater than 0 and less than 16 MPa$^{1/2}$.

15. The method according to claim 1, further comprising using at least one additional dye other than the at least one synthetic direct dye, wherein the at least one additional dye is chosen from:
   oxidation dyes or the addition salts thereof;
   dyes of natural origin; or
   mixtures thereof.

16. The method according to claim 1, further comprising using at least one chemical oxidizing agent chosen from hydrogen peroxide or hydrogen peroxide-generating systems.

17. The method according to claim 1, further comprising using at least one basifying agent chosen from i) (bi)carbonates, ii) aqueous ammonia, iii) alkanolamines, iv) oxyethylenated and/or oxypropylenated ethylenediamines, v) mineral or organic hydroxides, vi) alkali metal silicates, vii) amino acids, or viii) compounds of formula (II) below:

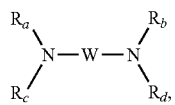
(II)

wherein, W is chosen from a divalent $(C_1-C_8)$alkylene radical optionally substituted with at least one hydroxyl group or at least one $(C_1-C_4)$alkyl radical and/or optionally interrupted with at least one heteroatom; $R_a$, $R_b$, $R_c$, $R_d$, and $R_e$, which may be identical or different, are chosen from a hydrogen atom or a $(C_1-C_4)$alkyl or hydroxy$(C_1-C_4)$alkyl radical.

18. The method according to claim 1, further comprising rinsing the fibers wherein the rinsing step is performed after the step of treating the fibers and before the step of dyeing the fibers, or after the step of dyeing the fibers and before the step of treating the fibers.

19. The method according to claim 1, comprising:
first, treating the fibers with the cosmetic composition Ci);
optionally, rinsing the fibers; and
then dyeing the fibers with the coloring composition Cii).

20. The method according to claim 1, wherein the cosmetic composition Ci) is left on the fibers for a time ranging from about 5 minutes to about 2 hours, at a temperature ranging from about 20° C. to about 50° C., and wherein the coloring composition Cii) is left on the fibers for a time ranging from about 1 minute to about 2 hours, at a temperature ranging from about 20° C. to about 50° C.

* * * * *